United States Patent
Markoutsa et al.

(10) Patent No.: US 11,911,481 B2
(45) Date of Patent: Feb. 27, 2024

(54) COMPOSITIONS AND METHODS FOR TREATING RSV-INFECTIONS

(71) Applicants: UNITED STATES GOVERNMENT AS REPRESENTED BY THE DEPARTMENT OF VETERANS AFFAIRS, Washington, DC (US); University of South Florida, Tampa, FL (US)

(72) Inventors: Eleni Markoutsa, Tampa, FL (US); Subhra Mohapatra, Tampa, FL (US); Shyam Mohapatra, Tampa, FL (US)

(73) Assignees: UNITED STATES GOVERNMENT AS REPRESENTED BY THE DEPARTMENT OF VETERANS AFFAIRS, Washington, DC (US); UNIVERSITY OF SOUTH FLORIDA, Tampa, FL (US)

( * ) Notice: Subject to any disclaimer, the term of this patent is extended or adjusted under 35 U.S.C. 154(b) by 740 days.

(21) Appl. No.: 17/057,153

(22) PCT Filed: May 21, 2019

(86) PCT No.: PCT/US2019/033245
§ 371 (c)(1),
(2) Date: Nov. 20, 2020

(87) PCT Pub. No.: WO2019/226612
PCT Pub. Date: Nov. 28, 2019

(65) Prior Publication Data
US 2021/0253422 A1 Aug. 19, 2021

Related U.S. Application Data

(60) Provisional application No. 62/674,396, filed on May 21, 2018.

(51) Int. Cl.
| | | |
|---|---|---|
| A61K 9/00 | (2006.01) | |
| A61K 9/127 | (2006.01) | |
| A61K 47/36 | (2006.01) | |
| C12N 15/113 | (2010.01) | |
| A61K 47/54 | (2017.01) | |
| A61K 47/69 | (2017.01) | |
| A61K 39/12 | (2006.01) | |
| A61K 45/06 | (2006.01) | |
| B82Y 5/00 | (2011.01) | |

(52) U.S. Cl.
CPC ............ *A61K 47/544* (2017.08); *A61K 39/12* (2013.01); *A61K 45/06* (2013.01); *A61K 47/6939* (2017.08); *B82Y 5/00* (2013.01); *C12N 15/1131* (2013.01); *C12N 2310/122* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 9,556,236 B1 * | 1/2017 | Mohapatra | ........... A61K 38/162 |
| 2013/0302407 A1 | 11/2013 | Rao et al. | |
| 2015/0037427 A1 | 2/2015 | Benita et al. | |
| 2015/0159171 A1 | 6/2015 | Deglon | |
| 2018/0037895 A1 | 2/2018 | Merzouki et al. | |

OTHER PUBLICATIONS

Baghdan et al. Lipid coated chitosan-DNA nanoparticles for enhanced gene delivery. International Journal of Pharmaceutics 535 (2018) 473-479.*
Channarong et al. Development and Evaluation of Chitosan-Coated Liposomes for Oral DNA Vaccine: The Improvement of Peyer's Patch Targeting Using a Polyplex-Loaded Liposomes. AAPS PharmSciTech, 2011, 12(1):192-200.*
Wang et al. Chitosan-coated liposomes for intracellular oligonucleotides delivery: Characteristics and cell uptake behavior. Drug Delivery, 2011; 18(3): 208-214.*
Baghdan et al. Lipid coated chitosan-DNA nanoparticles for enhanced gene delivery. Int J Pharm, Jan. 15, 2018, vol. 535, No. 1-2, pp. 473-479.
Wang, et al. Chitosan-coated liposomes for intracellular oligonucleotides delivery: characteristics and cell uptake behavior. Drug. Deliv, Apr. 2011, vol. 18, No. 3, pp. 208-214.
International Search Report and Written Opinion were dated Oct. 10, 2019 by the International Searching Authority for International Application No. PCT/US2019/033245, filed on May 21, 2019 and published as WO/2019/226612 on Nov. 28, 2019 (Applicant—The United States Government as Represented by the Department of Veterans Affairs) (19 Pages).
International Preliminary Report on Patentability was dated Nov. 24, 2020 by the International Searching Authority for International Application No. PCT/US2019/033245, filed on May 21, 2019 and published as WO/2019/226612 on Nov. 28, 2019 (Applicant—The United States Government as Represented by the Department of Veterans Affairs) (9 Pages).

* cited by examiner

*Primary Examiner* — Nianxiang Zou
(74) *Attorney, Agent, or Firm* — BALLARD SPAHR LLP

(57) ABSTRACT

This invention provides for a RSV-targeted nanoparticle PMN (RTPMN), combining HR2D anti-fusion peptide, and plasmid encoded siRNA against RSV-NS1 and/or RSV-P gene as a safe, effective and inexpensive anti-RSV prophylaxis and/or therapy.

32 Claims, 14 Drawing Sheets
Specification includes a Sequence Listing.

FIG. 2A
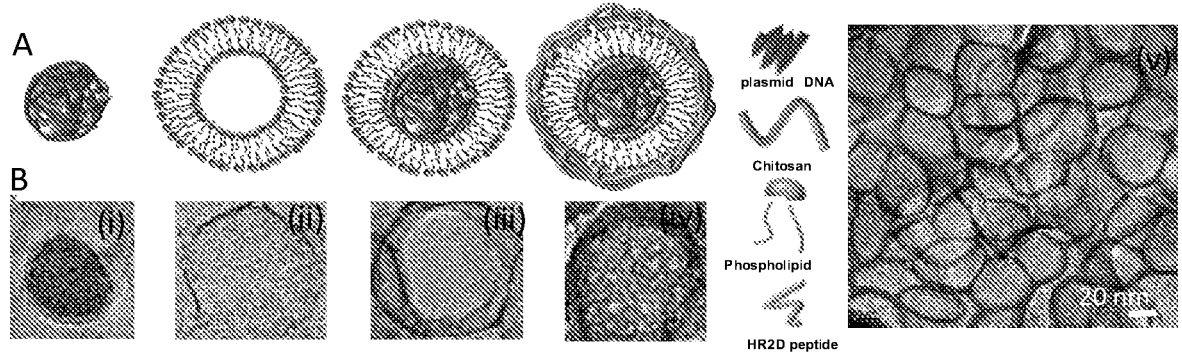
FIG. 2B
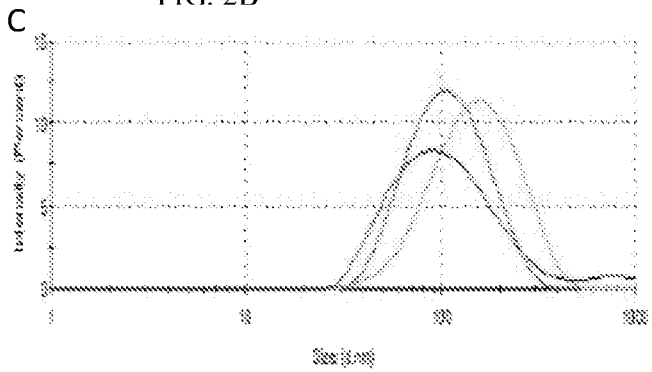
| Nanoparticle | Zeta potential (mV) |
|---|---|
| Chitosan-pDNA | +20.3 ± 1.2 |
| Liposomes | -7.5 ± 2.3 |
| Liposome coated Chitosan-pDNA | -5.4 ± 0.9 |
| Chitosan coated Liposomes (3-layer NPs) | +15.1 ± 2.6 |
FIG. 2C

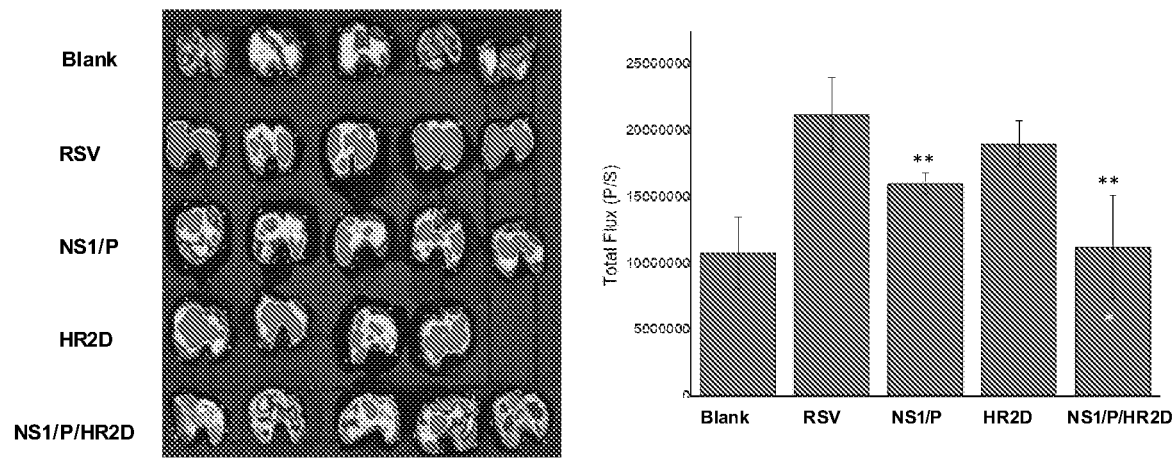
FIG. 13
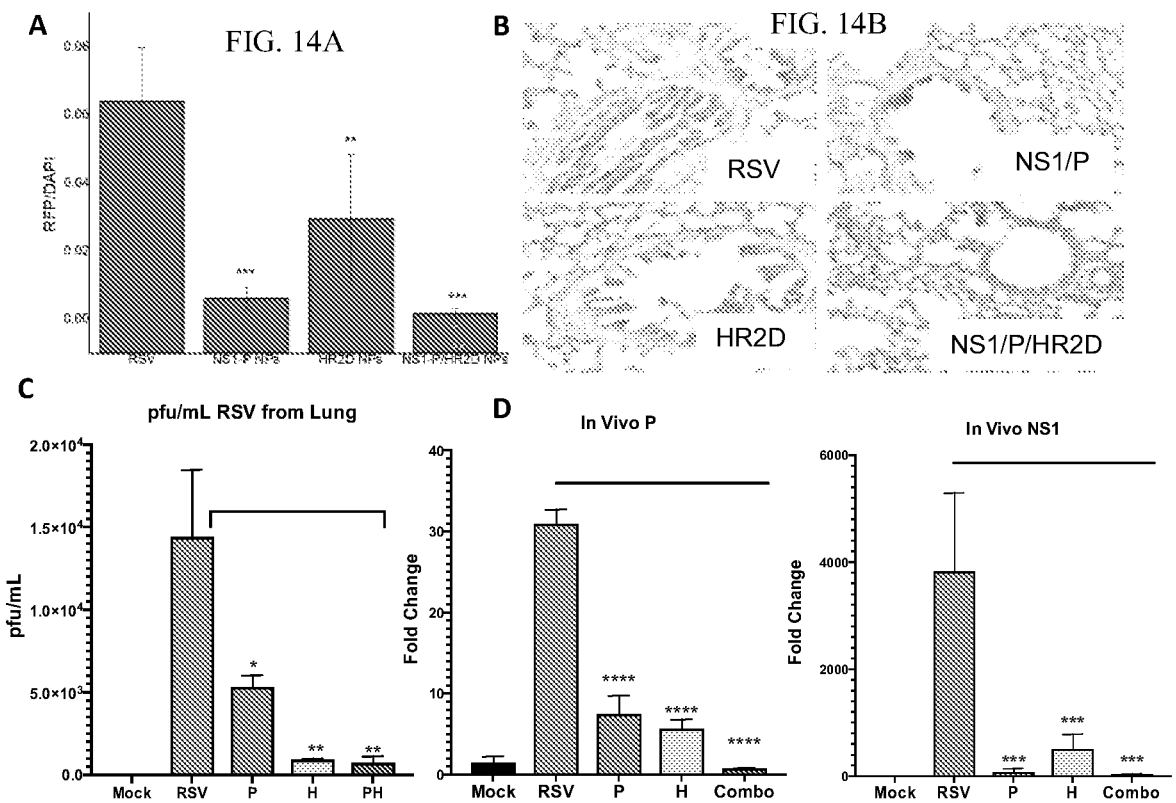
FIG. 14A
FIG. 14B
FIG. 14C
FIG. 14D

COMPOSITIONS AND METHODS FOR TREATING RSV-INFECTIONS

CROSS REFERENCE TO RELATED APPLICATIONS

This application claims the benefit of priority under 35 U.S.C. 371 of International Application No. PCT/US2019/033245, filed on May 21, 2019, which claims the benefit of the filing date of U.S. Provisional Application No. 62/674,396, which was filed on May 21, 2018. The content of these earlier filed applications is hereby incorporated by reference herein in its entirety.

INCORPORATION OF THE SEQUENCE LISTING

The present application contains a sequence listing that was submitted in ASCII format via EFS-Web concurrent with the filing of the application, containing the file name "37759_0063U2_SL.txt" which is 4,096 bytes in size, created on Nov. 19, 2020, and is herein incorporated by reference in its entirety pursuant to 37 C.F.R. § 1.52(e)(5).

BACKGROUND

Respiratory Syncytial Virus (RSV) is a potentially life-threatening respiratory pathogen that infects approximately 64 million children and immunocompromised adults globally. Currently, there is a need for prophylactic and therapeutic approaches effective against primary and secondary RSV infections. To date, approaches to vaccines or therapies involve either inhibiting the fusion of the virus to the mammalian cell or inhibition of replication of the virus within the cell. Thus, new compositions and methods effective against both primary and secondary RSV infections are needed.

SUMMARY

Disclosed herein are nanoparticles, comprising: (a) first layer comprising chitosan and a heptad repeat (HR)2 peptide; (b) a second layer comprising a plurality of phospholipids forming a lipid bilayer; and (c) a third layer comprising chitosan, and a vector comprising a nucleic acid; wherein the second layer is between the first layer and the third layer; wherein the first layer comprises an outer coat of the nanoparticle; and the third layer comprises an inner core of the nanoparticle.

Disclosed herein are methods of inhibiting respiratory syncytial virus (RSV) replication by disrupting, impairing and/or displacing the non-structural 1 protein (NS1)-phosphoprotein (P) interaction, the methods comprising contacting the nanoparticle described herein or a pharmaceutical composition described herein, with a cell.

Disclosed herein are pharmaceutically acceptable vaccine compositions comprising one or more of the nanoparticles described herein, wherein the nucleic acid is capable of eliciting an immune response in a host.

Disclosed herein are methods of vaccinating a mammal against a viral infection, the methods comprising administering one or more of the nanoparticles described herein, in a pharmaceutically acceptable formulation to a human subject.

Disclosed herein are methods of upregulating cellular interferon, the methods comprising contacting one or more of the nanoparticles described herein or a pharmaceutical composition described herein, with a cell.

Disclosed herein are methods of inhibiting the formation of mature RNA-dependent RNA polymerase, the methods comprising contacting one or more of the nanoparticles described herein or a pharmaceutical composition described herein, with a cell.

Disclosed herein are methods of upregulating cellular interferon in a subject, the methods comprising administering to the subject an effective amount of a pharmaceutical composition comprising one or more of the nanoparticles described herein.

Disclosed herein are methods of inhibiting the formation of mature RNA-dependent RNA polymerase in a subject, the methods comprising administering to the subject an effective amount of a pharmaceutical composition comprising one or more of the nanoparticles described herein.

Other features and advantages of the present compositions and methods are illustrated in the description below, the drawings, and the claims.

BRIEF DESCRIPTION OF THE DRAWINGS

FIG. 1 shows the agarose gel electrophoresis after restriction digest completed to analyze the success of the ligation reactions of the NS1 and P shRNA inserts into the plasmid backbone. Plasmid*—Final Ligated Plasmid with NS1 (6635 bp), P(6744 bp), or NS1/P (6744) shRNA inserted into vector backbone—Size of Control Plasmid: 6628; —NS1 insert (114 bp) is ligated between the KpnI and EcoRI sites; P insert (109 bp) is ligated within the PstI site. Digest*—K=KpnI (cuts at 930), E=EcoRI (cuts at 1037), P=PstI (cuts at 1435), X=XhoI (cuts at 2298).

FIGS. 2A-C show the preparation and characterization of nanoparticles to inhibit RSV infection. FIG. 2A shows the schematic representation of NP design. FIG. 2B shows the TEM images of Chitosan-pDNA nanoparticles (i), liposomes (ii), liposomes encapsulated chitosan nanoparticles (iii) and liposomes loaded with chitosan nanoparticles and coated with an outer layer of chitosan (iv) and (v). FIG. 2C shows the size distribution (DLS) and Zeta potential.

FIG. 3A shows the electrophoresis of Chitosan-DNA nanoparticles of different Chitosan:DNA ratios to determine plasmid encapsulation and integrity following synthesis. FIG. 3B shows HR2D peptide release from the outer chitosan NP-layer in PBS and in 10% FBS. FIG. 3C shows the results of the toxicity test of nanoparticles comprising different ratios of chitosan and lipid.

FIG. 13 shows the prophylactic potential of NS1-P/HR2D NPs. Fluorescent images of explanted lungs of mice administered with NS1-P NPS, HR2D NPs or NS1-P/HR2D NPs 2 days before RFP-RSV-Ln19-A2 infection. Mice were sacrificed 5 days post infection and the organs were imaged using IVIS system. RFP expression was quantified using imageJ.

FIGS. 14A-D show the prophylactic potential of NS1-P/HR2D NPs. Fluorescent analysis of lung sections of mice administered with NS1-P NPS, HR2D NPs or NS1-P/HR2D NPs 2 days before RSV inoculation. Mice were sacrificed 5 days post with RFP-RSV-Ln19-A2 inoculation. FIG. 14A shows the RFP to DAPI ratio. FIG. 14B shows the PAS staining. FIG. 14C shows the RSV plaque assay in vivo. FIG. 14D shows the RSV titers in vivo.

FIGS. 17A-D shows the preparation and characterization of nanoparticles that can inhibit RSV infection. FIG. 17A shows a schematic representation of nanoparticle design. FIG. 17B shows the TEM images of liposomes (left), Chitosan-pDNA nanoparticles (middle) and three-layer nanoparticles (right). FIG. 17C shows the size distribution (DLS). FIG. 17D shows the TEM image of three-layer nanoparticles.

DETAILED DESCRIPTION

Figure 1:
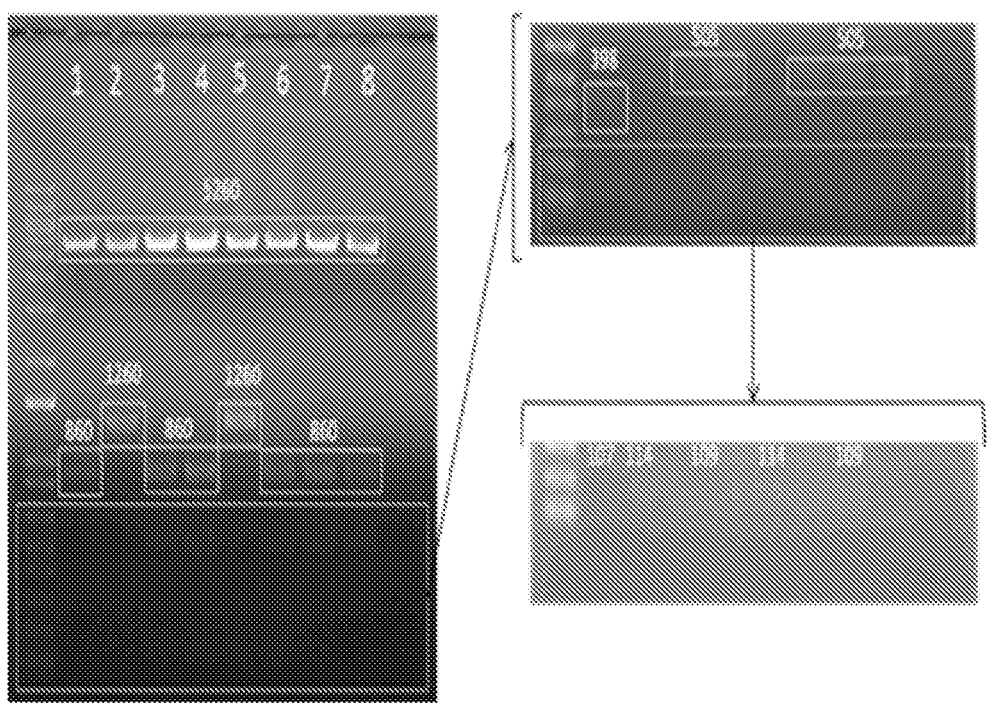
FIG. 1 shows the construction of the dual expressing short hairpin RNA recombinant plasmid. In particular.
Figure 3A:
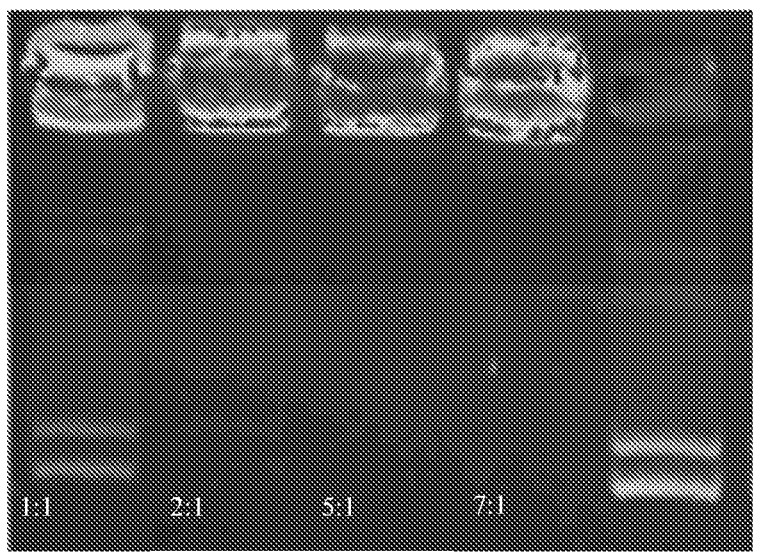
FIGS. 3A-C show DNA-encapsulation and HR2D-release.
Figure 3B:
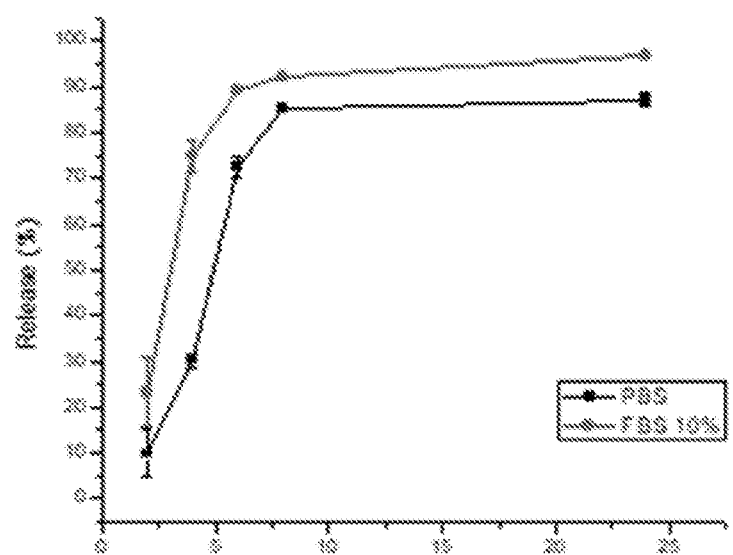
Figure 3C:
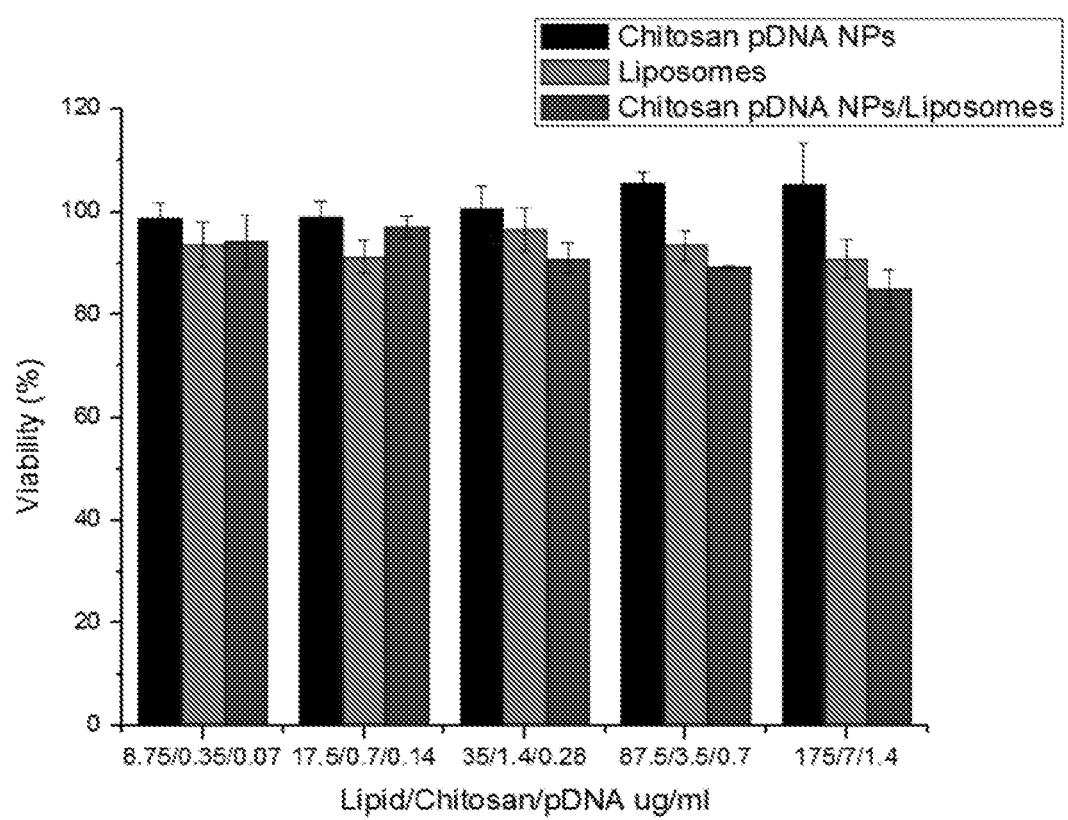
Figure 4:
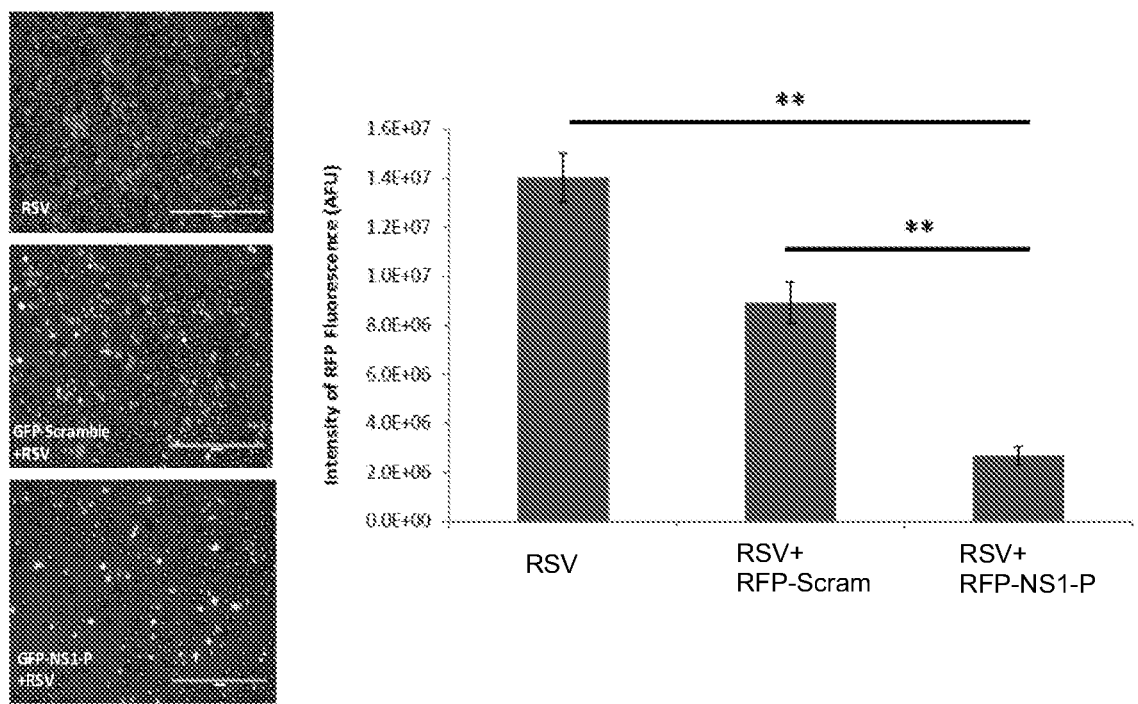
FIG. 4 shows inhibition of RSV rA2-L19F infection by plasmid construct expressing short-hairpin RNA for NS1 and P proteins. Fluorescent microscopy images of A549 cells or transfected A549 cells with GFP plasmid construct expressing short-hairpin RNA for NS1 and P proteins or scramble plasmid construct for 24 hours and infected with RFP-RSV-Ln19-A2 strain MOI 0.1 for 72 hours. RFP intensity quantified with ImageJ.
Figure 5:
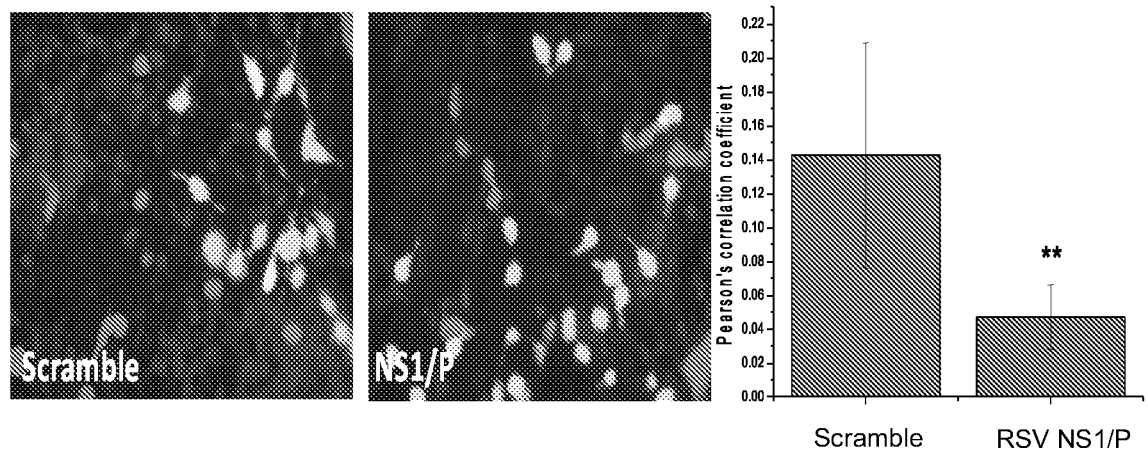
FIG. 5 shows inhibition of RSV rA2-L19F infection by a plasmid construct expressing short-hairpin RNA for NS1 and P proteins. Fluorescence microscopy images of HEK 293 cells transfected with GFP plasmid construct expressing short-hairpin RNA for NS1 and P proteins or scramble plasmid construct for 24 hours and infected with RFP-RSV-Ln19-A2 strain MOI 0.1 for 72 hours. Pearson correlation coefficient was estimated using Imagej-Fiji.
Figure 6:
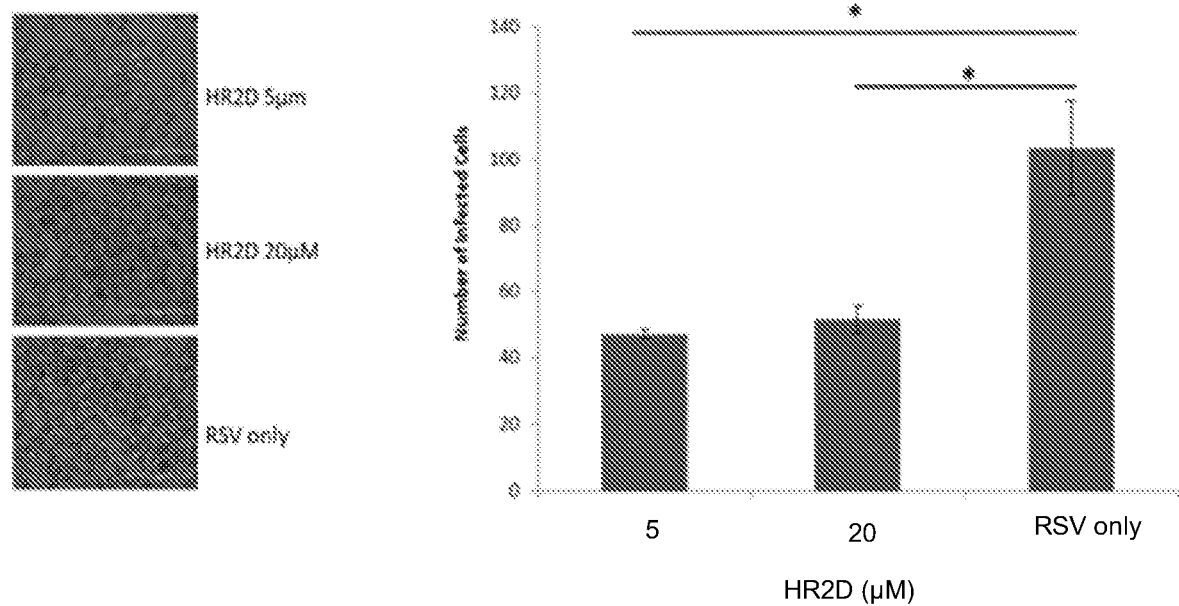
FIG. 6 shows inhibition of RSV rA2-L19F fusion by HR2D peptide. Fluorescence microscopy images of A549 cells pre-treated with 5 or 20 µM HR2D peptide 30 min before RFP-RSV-Ln19-A2 infection MOI 0.1 for 24 hours. RFP intensity quantified with ImageJ.
Figure 7:
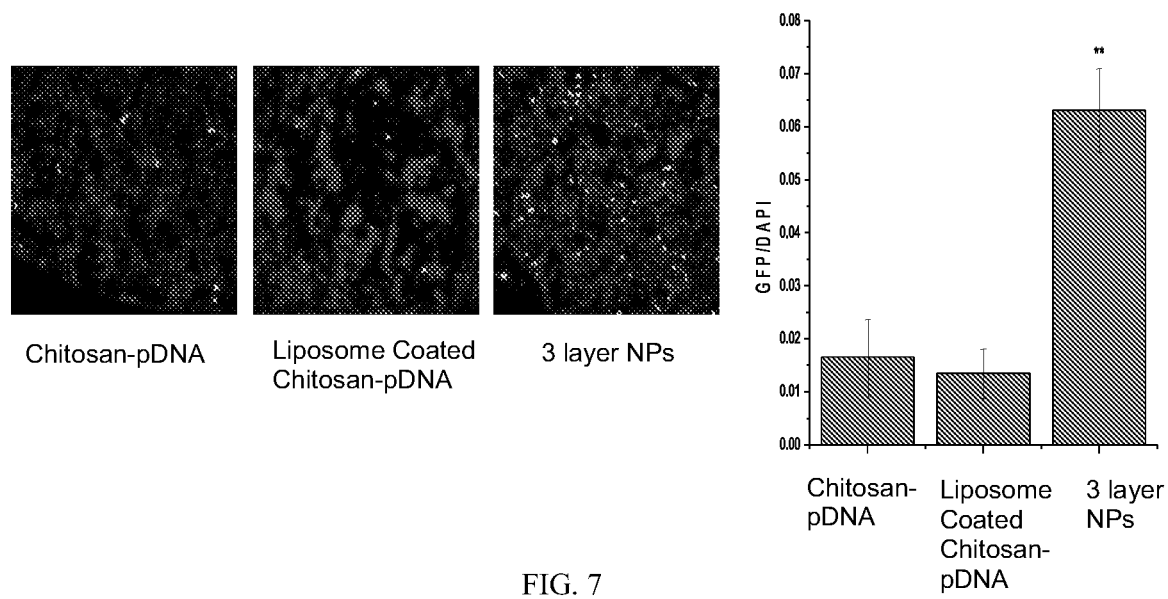
FIG. 7 shows the transfection efficiency of NPS. Fluorescence microscopy images of HEK 293 cells transfected with chitosan/GFP-pDNA, two layered nanoparticles and three layered nanoparticles for 24 hours.
Figure 8:
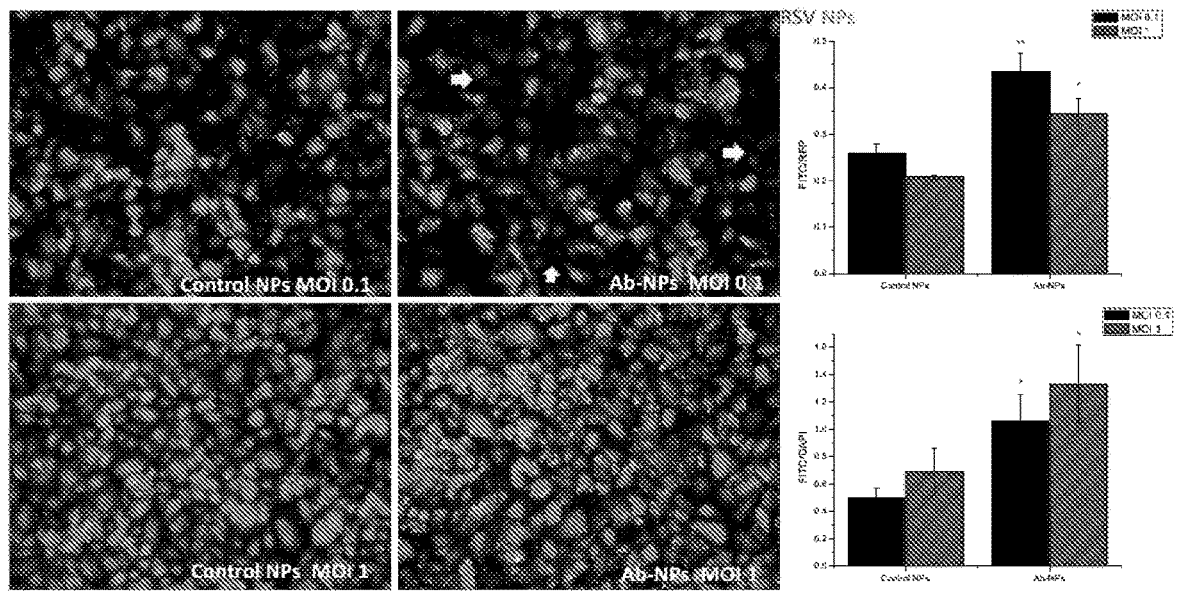
FIG. 8 shows the results of targeting NPs to RSV infected cells with anti-ICAM antibody. Fluorescence microscopy images of A549 cells infected with RFP-RSV-Ln19-A2 strain MOI 0.1 or MOI for 24 hours and treated with FITC-labeled targeted or control NPs for 1 hour. RFP and FITC intensity quantified with ImageJ.
Figure 9:
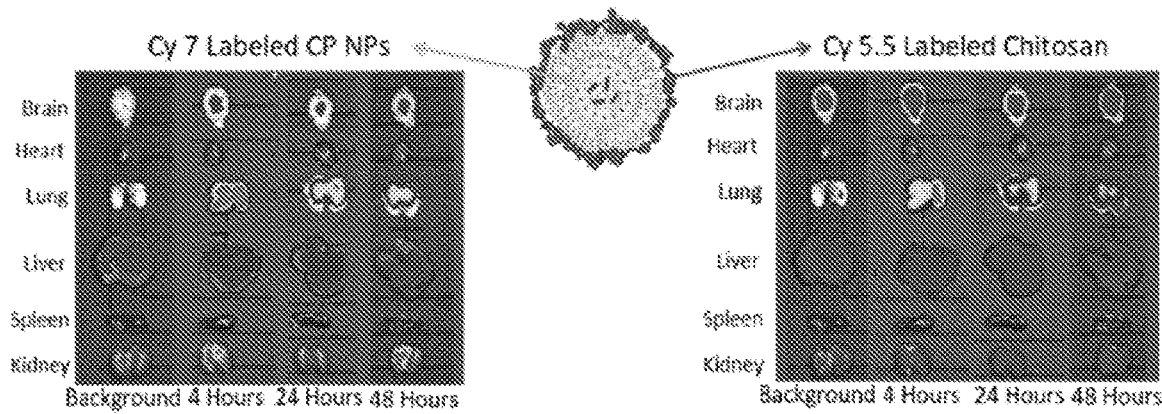
FIG. 9 shows the biodistribution of triple-layered NPs. Cy7 and Cy 5 images of explanted organs 4, 24 and 48 hours post-injection.
Figure 10:
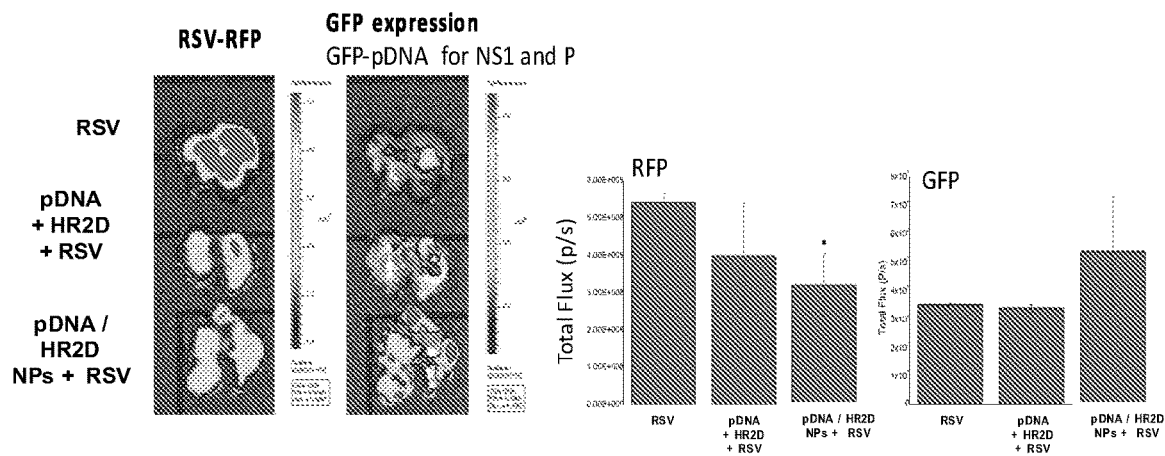
FIG. 10 shows the prophylactic potential of NS1-P/HR2D NPs. Fluorescent images of explanted lungs of mice administered with NS1-P/HR2D NPs or free NS1-P construct and HR2D 2 days before RSV inoculation. Mice were sacrificed 5 days post RFP-RSV-Ln19-A2 infection and the organs were imaged using IVIS system. RFP and GFP signal of lungs were quantified using imageJ.
Figure 11:
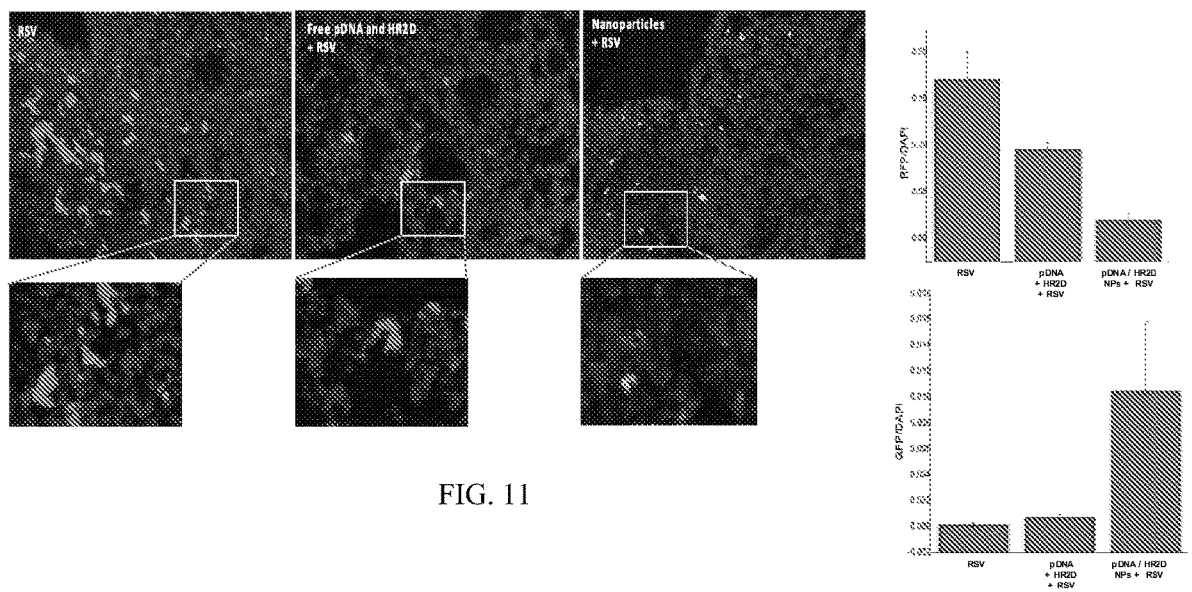
FIG. 11 shows the prophylactic potential of NS1-P/HR2D NPs. Fluorescence analysis of lung sections of mice administered with NS1-P-GFP/HR2D NPs or free NS1-P-GFP construct and HR2D 2 days before RSV infection and sacrificed 5 days post RFP-RSV-Ln19-A2 inoculation.
Figure 12:
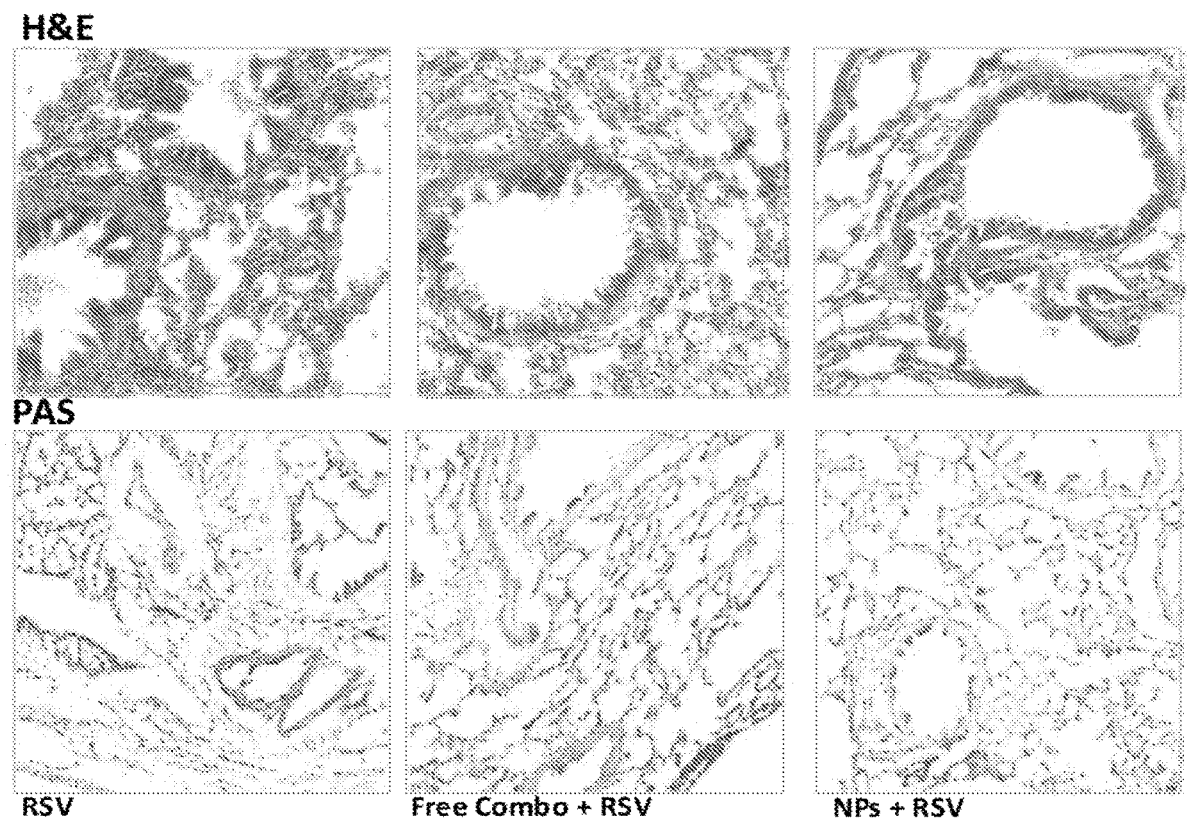
FIG. 12 shows the prophylactic potential of NS1-P/HR2D NPs. H&E and PAS staining of lung sections of mice administered with NS1-P-GFP/HR2D NPs or free NS1-P-GFP construct and HR2D 2 days before RSV infection. Mice were sacrificed 5 days post RFP-RSV-Ln19-A2 inoculation.
Figure 15:
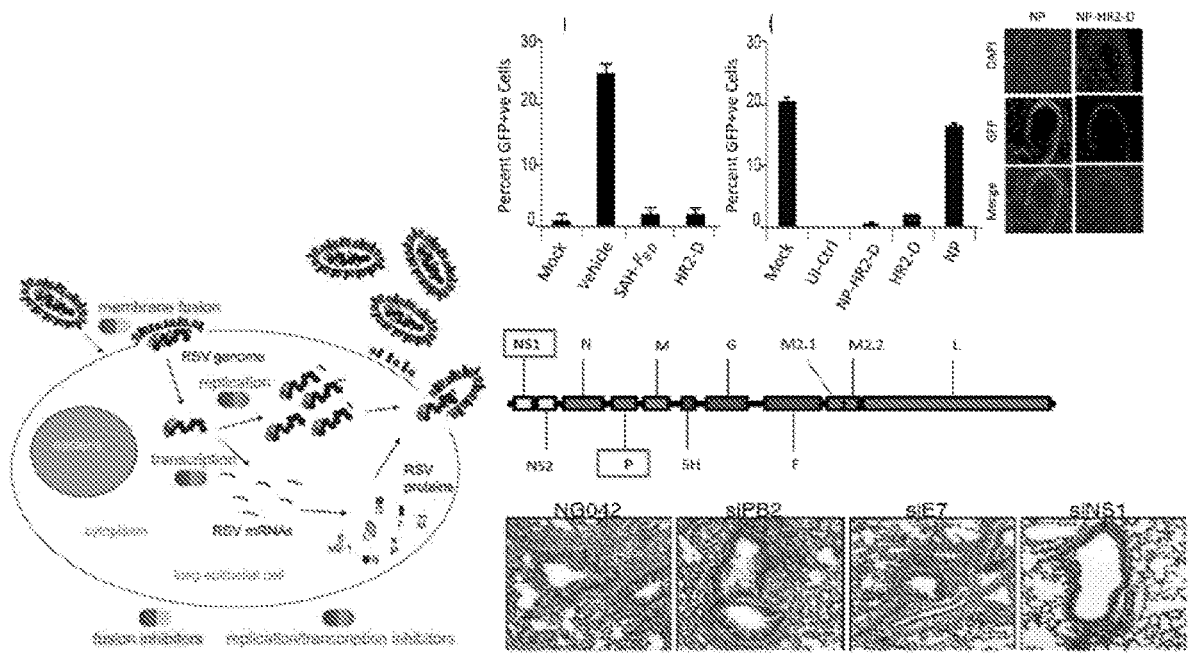
FIG. 15 shows inhibition of RSV fusion and replication: Transfection of shRNA encoded plasmid against RSV NS1 and P has a potent antiviral effect. This is augmented by the addition of anti-fusion peptide inhibitor HR2D. Delivery of these components via nanoparticle increases antiviral activity.
Figure 16:
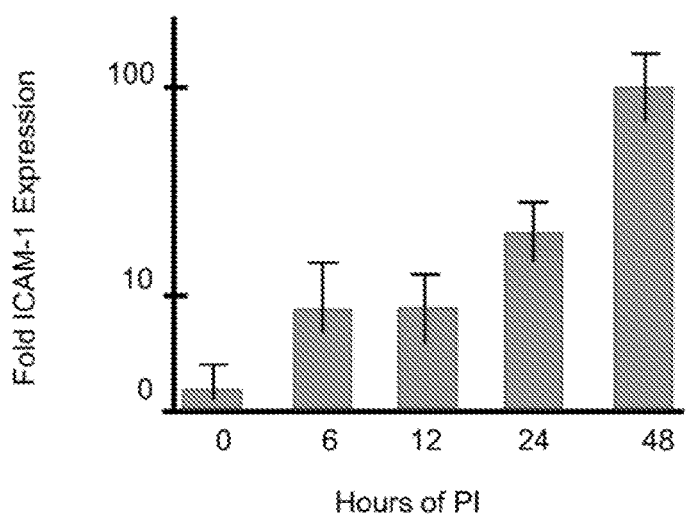
FIG. 16 shows the results of targeting RSV infected cells. ICAM-1 surface molecule is upregulated during RSV infection, and targeting of ICAM-1 by nanoparticles disclosed herein can be accomplished by using anti-ICAM-1 antibody.
Figures 17B, 17D:
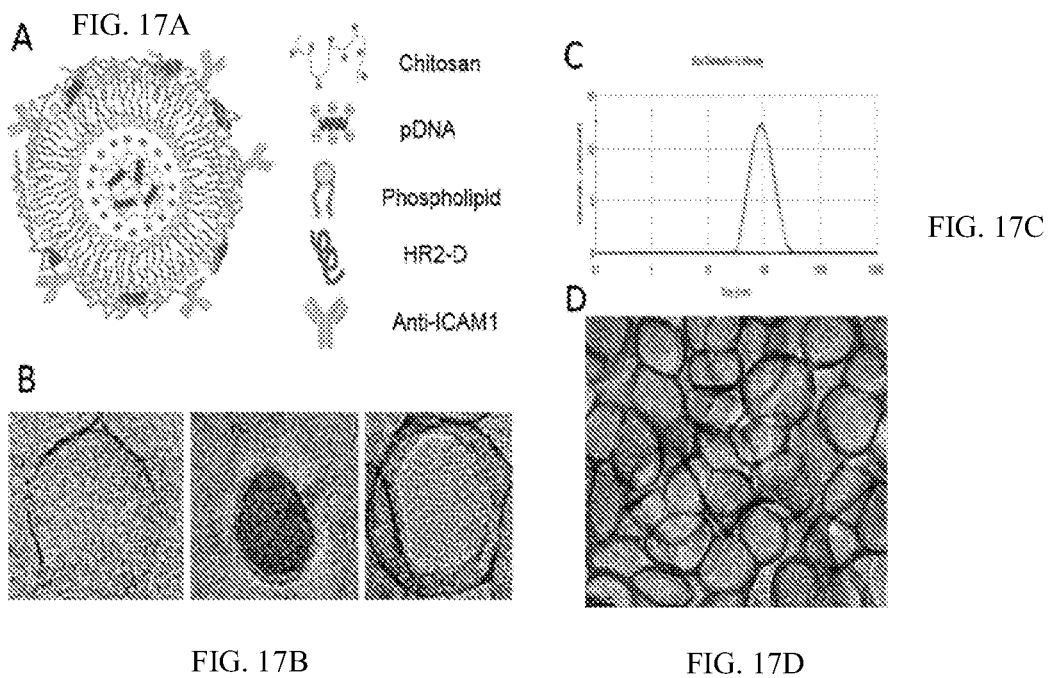
Figure 18:
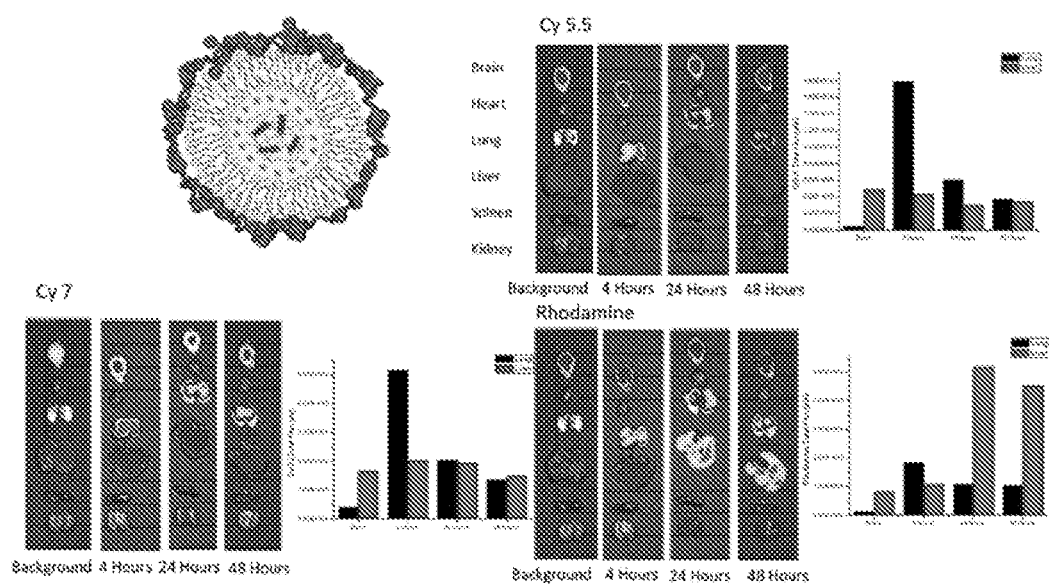
FIG. 18 shows the biodistribution of triple-layered NPs. Also shown are Cy7 and Cy 5 images of explanted organs 4, 24 and 48 hours post injection.
Figure 19:
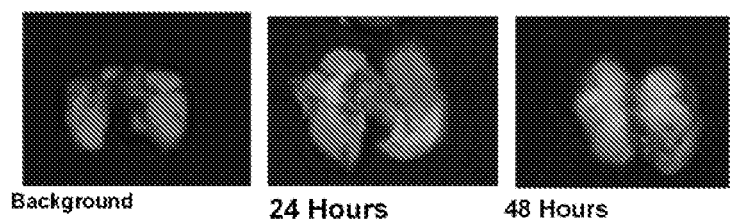
FIG. 19 shows lung-targeted transfection in vivo. Transfection of lungs with shRNA containing plasmid delivered by nanoparticle against RSV.

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

As used in the specification and the appended claims, the singular forms "a," "an" and "the" include plural referents unless the context clearly dictates otherwise.

The word "or" as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In some aspects, a subject can be a mammal. In some aspects, the subject can be a bovine. In some aspects, the subject can be a cow, heifer, bull, bullock, calf or an ox. In some aspects, the subject can be a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for an infection, such as, for example, prior to the administering step.

As used herein, the term "treating" or "treatment" refers to partially or completely alleviating, ameliorating, relieving, delaying onset of, inhibiting or slowing progression of, reducing severity of, and/or reducing incidence of one or more symptoms or features of, or otherwise prevent, hinder, retard, or reverse the progression of a particular disease, disorder, and/or condition or other undesirable symptom(s). Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. For example, the disease, disorder, and/or condition can be an RSV infection.

As used herein, the terms "disease" or "disorder" or "condition" are used interchangeably referring to any alternation in state of the body or of some of the organs, interrupting or disturbing the performance of the functions and/or causing symptoms such as discomfort, dysfunction, distress, or even death to the person afflicted or those in contact with a person. A disease or disorder or condition can also related to a distemper, ailing, ailment, malady, disorder, sickness, illness, complaint, affection.

The terms "vector" or "construct" refer to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. Moreover, the invention is intended to include other vectors which serve equivalent functions.

The term "expression vector" is herein to refer to vectors that are capable of directing the expression of genes to which they are operatively-linked. Common expression vectors of utility in recombinant DNA techniques are often in the form of plasmids. Recombinant expression vectors can comprise a nucleic acid as disclosed herein in a form suitable for expression of the acid in a host cell. In other words, the recombinant expression vectors can include one or more regulatory elements or promoters, which can be selected based on the host cells used for expression that is operatively linked to the nucleic acid sequence to be expressed.

"Modulate", "modulating" and "modulation" as used herein mean a change in activity or function or number. The change may be an increase or a decrease, an enhancement or an inhibition of the activity, function or number.

The terms "alter" or "modulate" can be used interchangeable herein referring, for example, to the expression of a nucleotide sequence in a cell means that the level of expression of the nucleotide sequence in a cell after applying a method as described herein is different from its expression in the cell before applying the method.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, in an aspect, the increase or promotion can be a 10, 20, 30, 40, 50, 60, 70, 80, 90, 100%, or more, or any amount of promotion in between compared to native or control levels. In an aspect, the increase or promotion is 10-20, 20-30, 30-40, 40-50, 50-60, 60-70, 70-80, 80-90, or 90-100% as compared to native or control levels. In an aspect, the increase or promotion is 0-25, 25-50, 50-75, or 75-100%, or more, such as 200, 300, 500, or 1000% more as compared to native or control levels. In an aspect, the increase or promotion can be greater than 100 percent as compared to native or control levels, such as 100, 150, 200, 250, 300, 350, 400, 450, 500% or more as compared to the native or control levels. As used herein, promoting can also mean enhancing.

As used herein, the term "inhibit" or "inhibiting" means to suppress, to hinder, to disrupt, to impair, to displace, or to impede. For example, a subject at risk for developing RSV or a subject with RSV may be administered an effective amount of a composition comprising nanoparticles of the present invention to inhibit the formation of mature RNA-dependent RNA polymerase.

As used herein, terms "prevention" or "preventing" can mean "acting before". In the context of a particular disease or health-related condition, these terms can refer to administration of an agent, drug, or remedy to a subject for the purpose of blocking the onset of disease, illness, infection, or health-related condition. For example, a subject at risk of developing RSV may be administered an effective amount of a composition comprising nanoparticles of the present invention to reduce the risk of development of the RSV compared to the risk in a subject that did not receive nanoparticles.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing disclosure has been described in some detail by way of illustration and example for purposes of clarity of understanding, certain changes and modifications may be practiced within the scope of the appended claims.

Respiratory Syncytial Virus Infection. RSV is the most frequent cause of pediatric bronchiolitis and elderly pneumonitis resulting in about 70,000-126,000 infant hospitalizations and 400 deaths, with about 62,000 RSV-associated hospitalizations reported annually in the U.S. for elderly over 64 years old. RSV is thought to contribute to about 64 million infections and 166,000 deaths worldwide. It is also considered the fourth leading cause of community pneumonia in elderly: Prevalence (7%): 11,000 death, 84% symptomatic, 74% URTI & 26% LRTI, 40% febrile. Currently, no effective vaccine or treatment is available.

Disclosed herein are nanoparticles that target both a viral fusion to a mammalian cell and the replication of the virus within the cell. The disclosed nanoparticles can provide an efficient prophylactic and therapeutic approach to treat primary and secondary respiratory syncytial virus (RSV) infections. To this end, a three-layer nanoparticle (NP) was designed. The surface layer of the nanoparticles can comprise chitosan loaded with a synthetic anti-fusion peptide (HR2-D) to inhibit the cellular internalization of RSV and consequently the infection. The core of the nanoparticles can comprise chitosan complexed with a dual expressing short hairpin RNA (shRNA) recombinant plasmid DNA. Both of shRNAs can be targeted to inhibit RSV replication. One shRNA can target the knockdown of RSV's non-structural 1 protein expression, which inhibits RSV replication and infection by upregulating cellular IFN. The second shRNA can target the knockdown of RSV's phosphoprotein expression, which inhibits RSV replication by the inhibiting the formation of the mature RNA-dependent RNA polymerase. A liposomal layer between the core and the shell of the nanoparticles can be used to stabilize and maintain the integrity of the plasmid DNA of the nanoparticles.

Disclosed herein are nanoparticles that were characterized for their size, shape, zeta potential and their pDNA encapsulation efficiency and release. In vitro studies confirmed the high transfection efficiency of this nanosystem. Biocompatibility studies revealed that in comparison with commonly used transfection reagents these NPs are much less toxic. Biodistribution studies revealed the accumulation and retention of NPs primarily to the lungs while the in vivo lung GFP expression confirmed the potential of this drug delivery system to knockdown gene expression and inhibit viral replication.

Compositions

Disclosed herein are nanoparticles for treating or preventing a respiratory syncytial virus (RSV) infection. In some aspects, the nanoparticles can comprise a first layer, a second, and a third layer. In some aspects, the nanoparticles can comprise a first layer, a second layer, a third layer, and a vector. In some aspects, the first layer can comprise chitosan and a heptad repeat (HR)2 peptide. In some aspects, the second layer can comprise a plurality of phospholipids forming a lipid bilayer. In some aspects, the third layer can comprise chitosan. In some aspects, the third layer can comprise chitosan and a vector. In some aspects, the third layer can comprise chitosan. In some aspects, the third layer can comprise chitosan and a vector comprising a nucleic acid. In some aspects, the vector can comprise a nucleic acid. In some aspects, the second layer can be between the first layer and the third layer. In some aspects, the first layer can comprise or form an outer coat of the nanoparticle. In some aspects, the third layer can comprise or form an inner core of the nanoparticle.

Disclosed herein are nanoparticles for treating or preventing a respiratory syncytial virus (RSV) infection. In some aspects, the nanoparticles are consisted of a first layer, a second, and a third layer. In some aspects, the first layer (shell) consist of chitosan and a heptad repeat (HR)2 peptide. In some aspects, the second layer (middle) consist of a plurality of phospholipids forming a lipid bilayer. In some aspects, the third layer (core) consist of chitosan complexed with the plasmid vector consisting of nucleic acids. In some aspects, the second layer can be between the first layer and the third layer. In some aspects, the first layer forms an outer coat of the nanoparticle.

Generally, chitosans are a family of cationic, binary hetero-polysaccharides. Chitosan is a derivative of chitin, produced by removing the acetate moiety from chitin. It is a polysaccharide, cationic, highly basic, mucoadhesive biocompatible polymer. More specifically, chitosan is a linear polysaccharide comprising randomly distributed β-(1→4)-linked D-glucosamine (deacetylated unit) and N-acetyl-D-glucosamine (acetylated unit). In some aspects, chitosan can be replaced with another cationic polymer or dendrimer.

In some aspects, chitosan, chitosan derivatives, or salts (e.g., nitrate, phosphate, sulphate, hydrochloride, glutamate, lactate or acetate salts) of chitosan may be used and are included within the meaning of the term "chitosan." As used herein, the term "chitosan derivatives" is intended to include ester, ether, or other derivatives formed by insertion of acyl and/or alkyl to chitosan. Examples are O-alkyl ethers of chitosan and O-acyl esters of chitosan. Modified chitosans, particularly those conjugated to polyethylene glycol, are also considered "chitosan derivatives." Many chitosans and their salts and derivatives are commercially available. Methods of preparing chitosans oligomers and their derivatives and salts are also known.

Chitosans can be obtained from any source known to those of ordinary skill in the art. For example, chitosans can be obtained from commercial sources. Chitosans can be obtained from chitin. Chitosan can be prepared by N-deacetylation of chitin. Chitosan is commercially available in a wide variety of molecular weight (e.g., 3-1000 kDa) and can have a degree of deacetylation ranging between 70%-90%.

In some aspects, the chitosan (or chitosan derivative or salt) can have a molecular weight of 4,000 Dalton or more. In some aspects, the molecular weight can be in the range 25,000 to 2,000,000 Dalton. In some aspects, the molecular weight can be about 50,000 to 300,000 Dalton. Chitosans of different molecular weights can be prepared by enzymatic degradation of high molecular weight chitosan using chitosanase or by the addition of nitrous acid. Both procedures are well known to those skilled in the art. Low molecular weight chitosan is water-soluble and can be produced from chitin by deacetylation to a degree of greater than 40%, between 50% and 98%, or between 70% and 90%.

In some aspects, the chitosan, chitosan derivative, or salt used herein can be water soluble. Chitosan glutamate is water soluble. By "water soluble" it is meant that that the chitosan, chitosan derivative, or salt dissolves in water at an amount of at least 10 mg/ml at room temperature and atmospheric pressure. The chitosan, chitosan derivative, or salt used in the present invention can have a positive charge.

In some aspects, the chitosan can be complexed with the HR2 peptide. For example, an ionic bond can be formed between the negatively charged HR2 peptide and the positively charged chitosan. In some aspects, the chitosan can be ionically bonded to the HR2 peptide.

In some aspects, the chitosan can be complexed with the plasmid (e.g., pDNA). In some aspects, the chitosan can be complexed with the pDNA using a coacervation method. Briefly, 0.25% chitosan can be dissolved in 1% acetic acid and then diluted 25 times in sodium acetate 5 mM. The pH can be adjusted to 5.5 using 2M sodium hydroxide. Plasmid DNA (20 μg/ml) can be prepared in 25 mM sodium sulfate. Equal volumes of chitosan solution and plasmid DNA can be mixed at 55° C. and vortexed for 1 minute.

In some aspects, the first layer can further comprise a targeting moiety. In some aspects, the targeting moiety can be an antibody. In some aspects, chitosan can be conjugated to one or more antibodies. In some aspects, the amine groups of the outer layer of chitosan can be conjugated to the carboxylic group of the antibody. In some aspects, the antibody can target (or be against) RSV protein F. In some aspects, the antibody can be an anti-F antibody. An anti-F antibody can be used to neutralize a virus. In some aspects, heparin sulfate can be complexed with the outer layer of chitosan to target RSV-infected cells. Heparin sulfate is negatively charged and can be complexed with chitosan during the formation of the outer layer. In some aspects, the antibody can be palivizumab (Synagis®). In some aspects, the antibody can target immune cells. In some aspects, the antibody can target leukocytes. In some aspects, the targeting moiety can be an anti-ICAM antibody.

Disclosed herein are HR2 derived peptides. Peptides derived from the HR1 and HR2 regions of the HIV-1 envelope glycoprotein gp41 have been shown to be effective inhibitors to prevent virus-host cell membrane fusion. A heptad repeat is example of a structural motif that consists of a repeating pattern of seven amino acids: a b c d e f g/H P P H C P C where H represents hydrophobic residues, C represents, typically, charged residues, and P represents polar residues. The positions of the heptad repeat are commonly denoted by the lowercase letters a through g. Examples of nonpolar (hydrophobic) amino acids are: glycine (G), alanine (A), valine (V), leucine (L), isoleucine (I), methionine (M), phenylalanine (F), tryptophan (W), proline (P). Examples of polar (hydrophilic) amino acids are: serine (S), threonine (T), cysteine (C), tyrosine (Y), asparagine (N), and glutamine (Q). Examples of electrically charged, negative and hydrophilic amino acids are: aspartic acid (D) and glutamic acid (E). Examples of electrically charged, positive and hydrophilic amino acids are: lysine (K), arginine (R), and histidine (H).

In some aspects, the HR2 peptide can be an anti-RSV-cell fusion peptide. In some aspects, the HR2 peptide can be an HR2D peptide. In some aspects, the HR2D peptide can be SEQ ID NO: 6. In some aspects, the HR2 peptide can be FDACISQVNECINQSLAFIRKSDELLHNVNAGKST (HR2-S; SEQ ID NO: 1). In some aspects, the HR2 peptide can be FDASISQVNEKINQSLAFICKSDELLCNVNAGKST (HR2-E; SEQ ID NO: 2). In some aspects, the HR2 peptide can be FDACISQVNECINQSLAFICKSDELLCNVNAGKST (HR2-A; SEQ ID NO: 3). In some aspects, the HR2 peptide can be GISQVNEGKSDELLG (HR2-B; SEQ ID NO: 4). In some aspects, the HR2 peptide can be GCISQVNECKSDELLCG (HR2-C; SEQ ID NO: 5). In some aspects, the HR2 peptide can be DACISQVNECINQSLAFICKSDELLCNT (HR2-D; SEQ ID NO: 6). In some aspects, the HR2 peptide consists of SEQ ID NO: 1, SEQ ID NO: 2, SEQ ID NO: 3, SEQ ID NO: 4, SEQ ID NO: 5, or SEQ ID NO: 6. In some aspects, the cysteine resides can form disulfide bonds. As the cysteine residues present in the HR2 or HR2D peptides disclosed herein are thiol-containing amino acids, they can form disulfide bonds after oxidation. In some aspects, the underlined glycine residues, GISQVNEGKSDELLG (HR2-B; SEQ ID NO: 4), GCISQVNECKSDELLCG (HR2-C; SEQ ID NO: 5), can be connected through glycine and flanked by a glycine residue at the N-terminal and C-terminal ends of the peptides.

In some aspects, the second layer of the nanoparticles described herein can further comprise small hydrophobic drugs or inhibitors. In some aspects, the small hydrophobic drug or inhibitor can be AZD 8797. For example, AZD 8797 can inhibit or block G-protein binding. The G-protein of RSV binds the CX3CR1 receptor. Thus, blocking the CX3CR1 receptor can reduce a viral infection. In some aspects, the small hydrophobic drugs or inhibitor can be incorporated into the lipid bilayer. In some aspects, the small hydrophobic drugs or inhibitor can be incorporated into the liposome layer. In some aspects, the second layer can comprise a plurality of liposomes or a liposome layer. Liposomes are composed of a lipid bilayer.

In some aspects, the third layer of the disclosed nanoparticles can comprise chitosan and a vector. In some aspects, the vector can comprise a nucleic acid. In some aspects, chitosan can be complexed with a nucleic acid. In some aspects, the chitosan can be complexed with DNA. In some aspects, the vector can be a plasmid encoding a short hairpin RNA (shRNA) or a small interfering RNA (siRNA). Short hairpin RNA or small hairpin RNA are artificial RNA molecules that comprising a hairpin turn that can be used to silence target gene expression. Expression of shRNA can be accomplished by delivery of plasmids through a vector. In some aspects, the vector or plasmid is complexed with the chitosan. In some aspects, the nucleic acid can be a shRNA or a siRNA. In some aspects, siRNA or the shRNA can be directed against RSV non-structural 1 protein (NS1) or RSV phosphoprotein (P). In some aspects, siRNA or the shRNA can be directed against RSV non-structural 1 protein (NS1) and RSV phosphoprotein (P). In some aspects, the siRNA or the shRNA can inhibit the expression of a gene that encodes RSV non-structural 1 protein (NS1) and phosphoprotein (P). In some aspects, the vector can be a dual expressing shRNA recombinant plasmid DNA. In some aspects, the vector can comprise a shRNA specific to RSV's non-structural 1 protein. In some aspects, the vector can comprise a shRNA specific to RSV's phosphoprotein. In some aspects, the vector can comprise a shRNA specific to RSV's non-structural 1 protein and a shRNA specific to a RSV phosphoprotein.

In some aspects, the shRNA disclosed herein can be directed against a sequence selected from one or more of the sequences of 5'-

(SEQ ID NO: 7)
CTGCTGTTGACAGTGAGCGAGGCAGCAATTCATTGAGTATGCTTGTGAAG

CCACAGATGAAGCATACTCAATGAATTGCTGCCCTGCCTACTGCCTCGGA

CTTCAAGGG-3' and 5'-

(SEQ ID NO: 8)
CTGCAGTGCTGTTGACAGTGAGCGACGATAATATAACAGCAAGATTGTGA

AGCCACAGATGAATCTTGCTGTTATATTATCGCTGCCTACTGCCTCGGAC

TTCAAGGCTGCA-3'.

In some aspects, the shRNA can comprise: 5'-

(NS1a; SEQ ID NO: 9)
AGCAGCAATTCATTGAGTATGCTAGTGAAGCCACAGATGTAGCATACTCA

ATGAATTGCTGCC-3';

5'-

(NS1b; SEQ ID NO: 10)
ATGCATGTTATTACAAGTAGTTTAGTGAAGCCACAGATGTAAACTACTTG

TAATAACATGCAC-3';

5'-

(Pa; SEQ ID NO: 11)
AGATAATATAACAGCAAGATTTAGTGAAGCCACAGATGTAAATCTTGCTG

TTATATTATCG-3';

or
5'-

(Pb; SEQ ID NO: 12)
ACAGGGAACAAGCCCAATTATTTAGTGAAGCCACAGATGTAAATAATTGG

GCTTGTTCCCTGC-3'.

Disclosed herein are compositions comprising a population of nanoparticles as described herein. In some aspects, the composition comprises $10^3$ to $10^{16}$, $10^4$ to $10^{15}$, $10^5$ to $10^{14}$, $10^6$ to $10^{14}$, $10^6$ to $10^{15}$ or $10^6$ to $10^{16}$ nanoparticles. In some aspects, the nanoparticles are comprised in a pharmaceutically acceptable carrier. In some aspects, the nanoparticles may, themselves be encapsulated in a coating, such as a pill or capsule. In some aspects, a coating for use in encapsulating particles can be a dissolvable coating.

Vectors can include plasmids, cosmids, and viruses (e.g., bacteriophage, animal viruses, and plant viruses), and artificial chromosomes (e.g., YACs). Vectors can comprise targeting molecules. A targeting molecule is one that directs the desired nucleic acid to a particular organ, tissue, cell, or other location in a subject's body. A vector, generally, brings about replication when it is associated with the proper control elements (e.g., a promoter, a stop codon, and a polyadenylation signal). Examples of vectors that are routinely used in the art include plasmids and viruses. The term "vector" includes expression vectors and refers to a vector containing a nucleic acid sequence coding for at least part of a gene product capable of being transcribed. A variety of ways can be used to introduce an expression vector into cells. In an aspect, the expression vector comprises a virus or an engineered vector derived from a viral genome. As used herein, "expression vector" is a vector that includes a regulatory region. A variety of host/expression vector combinations can be used to express the nucleic acid sequences disclosed herein. Examples of expression vectors include but are not limited to plasmids and viral vectors derived from, for example, bacteriophages, retroviruses (e.g., lentiviruses), and other viruses (e.g., adenoviruses, poxviruses, herpesviruses and adeno-associated viruses). Vectors and expression systems are commercially available and known to one skilled in the art.

In some aspects, the ratio of the chitosan complexed to the shRNA can be about 2 to about 10. In some aspects, the ratio of the chitosan complexed to the shRNA can be about 2, 5 or 7.

The nanoparticles disclosed herein can be formed to be of any size. In some aspects, the nanoparticles may be of a size in the range of about 3 nm to about 1000 nm in size or greater. In some aspects, the nanoparticles can be of a size in the range of about 1 μm to 1000 μm in size. If desired, particle size can be reduced using any method known to those of ordinary skill in the art. The particle size can be controlled using standard techniques, such as sonication and/or extrusion.

The nanoparticles disclosed herein can be stored using any method known to those of ordinary skill in the art. The nanoparticles can be stored at 4° C. until ready for use.

Disclosed herein are pharmaceutically acceptable vaccine compositions. In some aspects, the pharmaceutically acceptable vaccine composition can comprise any of the nanoparticles described herein. In some aspects, the nanoparticles can comprise a first layer, a second, and a third layer. In some aspects, the nanoparticles can comprise a first layer, a second, a third layer, and a vector. In some aspects, the first layer can comprise chitosan and a heptad repeat (HR)2 peptide. In some aspects, the second layer can comprise a plurality of phospholipids forming a lipid bilayer. In some aspects, the third layer can comprise chitosan. In some aspects, the vector can comprise a nucleic acid. In some aspects, the second layer can be between the first layer and the third layer. In some aspects, the nucleic acid is capable of eliciting an immune response in a host.

Methods of Treatment

Disclosed herein, are methods of delivering a nucleic acid to a subject. In some aspects, can comprise administering to the subject an effective amount of a pharmaceutical composition comprising any of the nanoparticles described herein. In some aspects, the method can further comprise identifying a subject in need thereof. In some aspects, the subject can be a human. In some aspects, the subject can be a bovine. In some aspects, the subject can be a cow, heifer, bull, bullock, calf or an ox. In some aspects, the subject has RSV. In some aspects, the composition can be delivered to the subject intranasally, orally, by injection, or intravenously. In some aspects, the method can further comprise administering one or more therapeutic agents. In some aspects, a therapeutic agent can be administered to a subject for the purpose of obtaining a therapeutic benefit of a disease, infection, illness, or health-related condition. In some aspects, the therapeutic agent can be an antiviral agent, an antibody, a corticosteroid, an antibiotic or a combination thereof. In some aspects, the antiviral agent can be ribavirin. In some aspects, the antibody can be palivizumab (Synagis®). In some aspects, the therapeutically effective amount of any of the compositions or nanoparticles described herein can be administered before, during or after administration of an antiviral agent, an antibody, a corticosteroid, an antibiotic or a combination thereof.

Disclosed herein, are method of treating or preventing a respiratory syncytial virus infection in a subject. In some aspects, the method can comprising administering to the subject an effective amount of a pharmaceutical composition comprising any of the nanoparticles described herein. In some aspects, the method can further comprise identifying a subject in need thereof. In some aspects, the subject can be a human. In some aspects, the subject can be a bovine. In some aspects, the subject can be a cow, heifer, bull, bullock, calf or an ox. In some aspects, the subject has RSV. In some aspects, the composition can be delivered to the subject intranasally, orally, by injection, or intravenously. In some aspects, the method can further comprise administering one or more therapeutic agents. In some aspects, the therapeutic agent can be antiviral agent, an antibody, a corticosteroid, an antibiotic or a combination thereof. In some aspects, the antiviral agent can be ribavirin. In some aspects, the antibody can be palivizumab (Synagis®). In some aspects, the therapeutically effective amount of any of the compositions or nanoparticles described herein can be administered before, during or after administration of an antiviral agent, an antibody, a corticosteroid, an antibiotic or a combination thereof.

Disclosed herein are methods of inhibiting respiratory syncytial virus (RSV) replication. In some aspects, the method of inhibiting RSV replication can be by disrupting, impairing and/or displacing the non-structural 1 protein (NS1)-phosphoprotein (P) interaction. In some aspects, the method can comprise contacting the nanoparticle described herein with a cell. In some aspects, the method can comprise contacting the pharmaceutical composition described herein with a cell.

Disclosed herein are methods of vaccinating a mammal against a viral infection. In some aspects, the method can comprise administering a nanoparticle described herein, in a pharmaceutically acceptable formulation to a human subject. In some aspects, the mammal can be a bovine. In some aspects, the mammal can be a cow, heifer, bull, bullock, calf or an ox.

Disclosed herein are methods of upregulating cellular interferon. In some aspects, the method can comprise contacting any of the nanoparticles disclosed herein with a cell. In some aspects, the method can comprise contacting the pharmaceutical composition described herein with a cell.

Disclosed herein are methods of inhibiting the formation of mature RNA-dependent RNA polymerase. In some aspects, the method can comprise contacting any of the nanoparticles disclosed herein with a cell. In some aspects, the method can comprise contacting the pharmaceutical composition disclosed herein with a cell.

Disclosed herein are methods of upregulating cellular interferon in a subject. In some aspects, the method can comprising administering to the subject an effective amount of a pharmaceutical composition comprising any of the nanoparticles disclosed herein. In some aspects, the method can further comprise identifying a subject in need thereof. In some aspects, the subject can be a human. In some aspects, the subject can be a bovine. In some aspects, the subject can be a cow, heifer, bull, bullock, calf or an ox. In some aspects, the subject has RSV. In some aspects, the composition can be delivered to the subject intranasally, orally, by injection, or intravenously. In some aspects, the method can further comprise administering one or more therapeutic agents. In some aspects, the therapeutic agent can be antiviral agent, an antibody, a corticosteroid, an antibiotic or a combination thereof. In some aspects, the antiviral agent can be ribavirin. In some aspects, the antibody can be palivizumab (Synagis®). In some aspects, the therapeutically effective amount of any of the compositions or nanoparticles described herein can be administered before, during or after administration of an antiviral agent, an antibody, a corticosteroid, an antibiotic or a combination thereof.

Disclosed herein are method of inhibiting the formation of mature RNA-dependent RNA polymerase in a subject. In some aspects, the method can comprising administering to the subject an effective amount of a pharmaceutical composition comprising any of the nanoparticles disclosed herein. In some aspects, the method can further comprise identifying a subject in need thereof. In some aspects, the subject can be a human. In some aspects, the subject can be a bovine. In some aspects, the subject can be a cow, heifer, bull, bullock, calf or an ox. In some aspects, the subject has RSV. In some aspects, the composition can be delivered to the subject intranasally, orally, by injection, or intravenously. In some aspects, the method can further comprise administering one or more therapeutic agents. In some aspects, the therapeutic agent can be an antiviral agent, an antibody, a corticosteroid, an antibiotic or a combination thereof. In some aspects, the antiviral agent can be ribavirin. In some aspects, the antibody can be palivizumab (Synagis®). In some aspects, the therapeutically effective amount of any of the compositions or nanoparticles described herein can be administered before, during or after administration of an antiviral agent, an antibody, a corticosteroid, an antibiotic or a combination thereof.

The compositions described herein can be formulation in a variety of combinations. The particular combination of any of the nanoparticles disclosed herein with an antiviral agent, an antibody, a corticosteroid, an antibiotic or a combination thereof can vary according to many factors, for example, the particular the type and severity of the RSV.

The compositions described herein can be administered to the subject (e.g., a human patient or a mammal) in an amount sufficient to delay, reduce, or preferably prevent the onset of clinical disease. Accordingly, in some aspects, the patient can be a human patient. In an aspect, the human subject or patient can be a child or an adult. In therapeutic applications, compositions can be administered to a subject (e.g., a human patient) already with or diagnosed with RSV in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a composition (e.g., a pharmaceutical composition) can be an amount that achieves a cure, but that outcome is only one among several that can be achieved. As noted, a therapeutically effective amount includes amounts that provide a treatment in which the onset or progression of the RSV is delayed, hindered, or prevented, or the RSV or a symptom of the RSV is ameliorated. One or more of the symptoms can be less severe. Recovery can be accelerated in an individual who has been treated.

In some aspects, the RSV can be strain A or strain B. In some aspects, the RSV can be a primary infection. In some aspects, the RSV can be a secondary infection. RSV is a syncytial virus causing respiratory tract infections. Human respiratory syncytial virus is a medium-sized (120-200 nm) enveloped virus that contains a lipoprotein coat and a linear negative-sense RNA genome. The former contains virally encoded F, G, and SH lipoproteins. The F and G lipoproteins are the two that target the cell membrane, and are highly conserved among RSV isolates. HRSV is divided into two antigenic subgroups, A and B, on the basis of the reactivity of the virus with monoclonal antibodies against the attachment (G) and fusion (F) glycoproteins. Subtype B is characterized as the asymptomatic strains of the virus that the majority of the population experiences. The more severe clinical illnesses involve subtype A strains, which tend to predominate in most outbreaks.

The incubation time (from infection until symptoms arrive) can be about 4 to 5 days. For adults, RSV can produces symptoms, often indistinguishable from common colds and minor illnesses. Other RSV symptoms include but are not limited to listlessness, poor or diminished appetite, and a fever.

Disclosed herein, are methods of treating a subject with RSV or suspected of having RSV. The RSV can be any strain of RSV. In some aspects, the subject has been diagnosed with RSV prior to the administering step.

Pharmaceutical Compositions

As disclosed herein, are pharmaceutical compositions, comprising any of the nanoparticles described herein and a pharmaceutical acceptable carrier described herein. In some aspects, compositions and nanoparticles can be formulated for oral or parental administration. In an aspect, the parental administration can be intravenous, subcutaneous, intramuscular or direct injection. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

Pharmaceutically acceptable carriers and excipients can be incorporated (e.g., water, saline, aqueous dextrose, and glycols, oils (including those of petroleum, animal, vegetable or synthetic origin), starch, cellulose, talc, glucose, lactose, sucrose, gelatin, malt, rice, flour, chalk, silica gel, magnesium stearate, sodium stearate, glycerol monosterate, sodium chloride, dried skim milk, glycerol, propylene glycol, ethanol, and the like). The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in "Remington's Pharmaceutical Sciences" by E. W. Martin, which is herein incorporated by reference. Such compositions will, in any event, contain an effective amount of the compositions together with a suitable amount of carrier so as to prepare the proper dosage form for proper administration to the patient.

Pharmaceutically acceptable carrier can also include any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated. The compositions used in the present invention may comprise different types of carriers depending on whether it is to be administered in solid, liquid or aerosol form, and whether it need to be sterile for such routes of administration as injection.

The formulation of the composition may vary depending upon the route of administration. For parenteral administration in an aqueous solution, for example, the solution should be suitably buffered if necessary and the liquid diluent first rendered isotonic with sufficient saline or glucose. In this connection, sterile aqueous media which can be employed will be known to those of skill in the art in light of the present disclosure.

The compositions can be formulated in various ways for parenteral or nonparenteral administration. Where suitable, oral formulations can take the form of tablets, pills, capsules, or powders, which may be enterically coated or otherwise protected. Sustained release formulations, suspensions, elixirs, aerosols, and the like can also be used.

In some aspects, the nanoparticles disclosed herein can be formulated for intravenous administration, intranasal administration, intratracheal administration, intramuscular administration, subcutaneous administration, intranasal administration, oral administration, by inhalation or for direct injection or intravenous perfusion.

In some aspects, the composition or nanoparticle described herein can be administered intravenously, intradermally, intraarterially, intraperitoneally, intratracheally, intravitreally, intramuscularly, intraperitoneally, subcutaneously, mucosally, locally, by injection, by infusion, by continuous infusion, by localized perfusion bathing target cells directly, via a catheter, or via a lavage. For example, the composition may be administered by injection or infusion. In some aspects, the perfusion can be intravenous perfusion.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules.

In addition to the compositions formulated for parenteral administration, such as intravenous or intramuscular injection, other pharmaceutically acceptable forms include, formulations for administration via an implantable drug delivery device, and any other form. Also disclosed herein are nasal solutions or sprays, aerosols or inhalants.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like).

In some aspects, a pharmaceutical composition can include at least about 0.1% by weight of the active agent. The composition may include, for example, about 0.01%. In some aspects, the pharmaceutical composition can include about 2% to about 75% of the weight of the composition, or between about 25% to about 60% by weight of the composition, for example, and any range derivable therein.

In some aspects, the pharmaceutical composition can comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. The composition must be stable under the conditions of manufacture and storage, and preserved against the contaminating action of microorganisms, such as bacteria and fungi. It will be appreciated that exotoxin contamination should be kept minimally at a safe level, for example, less than 0.5 ng/mg protein.

In some aspects, where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. In some aspects, the compositions can include isotonic agents, such as, for example, sugars, sodium chloride or combinations thereof.

Disclosed herein are nasal solutions or sprays, aerosols or inhalants comprising the nanoparticles described herein. Nasal solutions can be aqueous solutions designed to be administered to the nasal passages in drops or sprays.

Disclosed herein are sterile injectable solutions that can be prepared by incorporating the nanoparticles in the required amount in the appropriate solvent with various of the other ingredients described herein, followed by sterilization.

In an aspect, compositions or nanoparticles can be administered systemically. In an aspect, the compositions or nanoparticles can be administered intravenously. In an aspect, the pharmaceutical composition can be formulated for systemic or intravenous administration.

The nanoparticles can be administered to the subject using any method known to those of ordinary skill in the art. For example, a pharmaceutically effective amount of a composition comprising the nanoparticles described herein can be administered intravenously, intradermally, intraarterially, intraperitoneally, intralesionally, intratracheally, intranasally, topically, intramuscularly, intraperitoneally, subcutaneously, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990). In some aspects, the compositions can be administered to a subject using a drug delivery device.

The compositions described herein can be formulated to include a therapeutically effective amount of any of the nanoparticles described herein. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to RSV.

The compositions described herein can be formulated to include a therapeutically effective amount of the nanoparticles disclosed herein alone or in combination with one or more of the therapeutic agents disclosed herein. In an aspect, the nanoparticles can be contained within a pharmaceutical formulation. In an aspect, the pharmaceutical formulation can be a unit dosage formulation.

The therapeutically effective amount or dosage of any of the nanoparticles or compositions used in the methods as disclosed herein applied to mammals (e.g., humans, bovine) can be determined by one of ordinary skill in the art with consideration of individual differences in age, weight, sex, other drugs administered and the judgment of the attending clinician. Variations in the needed dosage may be expected. Variations in dosage levels can be adjusted using standard empirical routes for optimization. The particular dosage of a pharmaceutical composition to be administered to the patient will depend on a variety of considerations (e.g., the severity of the cancer symptoms), the age and physical characteristics of the subject and other considerations known to those of ordinary skill in the art. Dosages can be established using clinical approaches known to one of ordinary skill in the art.

For example, a dose of the nanoparticles (and/or therapeutic agent) can be about 0.0001 milligrams to about 1.0 milligrams, or about 0.001 milligrams to about 0.1 milligrams, or about 0.1 milligrams to about 1.0 milligrams, or even about 10 milligrams per dose or so. Multiple doses can also be administered. In some aspects, a dose can be at least about 0.0001 milligrams. In some aspects, a dose can be at least about 0.001 milligrams. In some aspects, a dose can be at least 0.01 milligrams. In some aspects, a dose can be at least about 0.1 milligrams. In some aspects, a dose can be at least 1.0 milligrams. In some aspects, a dose can be at least 10 milligrams. In some aspects, a dose can be at least 100 milligrams or higher.

In some aspects, a dose can also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In some aspects, a range of about 5 mg/kg/body weight to about 100 mg/kg/body weight, about 5 microgram/kg/body weight to about 500 milligram/kg/body weight, etc., can be administered.

The duration of treatment with any composition provided herein can be any length of time from as short as one day to as long as the life span of the host (e.g., many years). The dose can be repeated as needed as determined by those of ordinary skill in the art. Thus, in some aspects, a single dose can be administered. In some aspects, multiple (two or more) doses can be administered. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges. For example, the compositions can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present compositions can be administered once (or twice, three times, etc.) daily, weekly, monthly, or yearly.

The amount or dose specified can be the amount or dose administered as the average daily, average weekly, or average monthly dose, or it may be expressed in terms of mg/kg, where kg refers to the weight of the patient and the mg is specified above. In other aspects, the amount specified can be any number described herein. A clinician can readily determine the effective amount of the composition needed to inhibit or prevent RSV replication, by taking into account factors, such as the size and weight of the subject; the extent of disease penetration; the age, health and sex of the subject; the route of administration; and whether the administration is regional or systemic.

The total effective amount of the compositions as disclosed herein can be administered to a subject as a single dose, either as a bolus or by infusion over a relatively short period of time, or can be administered using a fractionated treatment protocol in which multiple doses are administered over a more prolonged period of time. Alternatively, continuous intravenous infusions sufficient to maintain therapeutically effective concentrations in the blood are also within the scope of the present disclosure.

The compositions described herein can be administered in conjunction with other therapeutic modalities to a subject in need of therapy. The nanoparticles and compositions disclosed herein can be given prior to, simultaneously with or after treatment with other agents or regimes.

The interval between the administration of the nanoparticles and the secondary therapy can be any interval as determined by those of ordinary skill in the art. For example, the interval can be minutes to weeks. In some aspects, where the agents are separately administered, one would generally ensure that a significant period of time did not expire between the time of each delivery, such that each therapeutic agent would still be able to exert an advantageously combined effect on the subject. For example, the interval between therapeutic agents may be about 12 h to about 24 h of each other and, more preferably, within about 6 hours to about 12 h of each other. In some aspects, it may be desirable to extend the time period for treatment significantly, however, where several days (2, 3, 4, 5, 6 or 7) to several weeks (1, 2, 3, 4, 5, 6, 7 or 8) lapse between the respective administrations. In some aspects, the timing of administration of a secondary therapeutic agent can be determined based on the response of the subject to the nanoparticles.

Articles of Manufacture

The composition described herein can be packaged in a suitable container labeled, for example, for use as a therapy to treat cancer or any of the methods disclosed herein. Accordingly, packaged products (e.g., sterile containers containing the composition described herein and packaged for storage, shipment, or sale at concentrated or ready-to-use concentrations) and kits, including any of the nanoparticles as described herein and instructions for use, are also within the scope of the disclosure. A product can include a container (e.g., a vial, jar, bottle, bag, or the like) containing the composition described herein. In addition, an article of manufacture further may include, for example, packaging materials, instructions for use, syringes, buffers or other control reagents for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the composition therein should be administered (e.g., the frequency and route of administration), indications therefor, and other uses. The composition can be ready for administration (e.g., present in dose-appropriate units), and may include a pharmaceutically acceptable adjuvant, carrier or other diluent. Alternatively, the composition can be provided in a concentrated form with a diluent and instructions for dilution.

In an aspect, the kits can include one or more of the nanoparticles; expression vectors comprising nucleic acid sequences encoding one or more of the shRNA sequences. The kit can include one or more pharmaceutically acceptable carriers. In addition, devices or materials for administration of the nanoparticles (e.g., syringes, needles, etc.) can also be included.

EXAMPLES

Example 1: Construct Recombinant shRNA-Plasmid

Disclosed herein is a dual expressing short hairpin RNA (shRNA) recombinant plasmid that will induce RNA interference. One shRNA is targeted for knockdown of RSV's non-structural 1 (NS1) protein, which antagonizes the host interferon (IFN) production. NS1 knockdown inhibits RSV replication and infection by upregulating cellular IFN and apoptosis due to the consequential knockdown of mitochondrial antiviral signaling (MAVS). The second shRNA is targeted for the knockdown of RSV's phosphoprotein (P), which plays the role as a component of the viral RNA-dependent RNA polymerase (RDRP).

The sequence of NS1 is: 5'-

(SEQ ID NO: 7)
CTGCTGTTGACAGTGAGCGAGGCAGCAATTCATTGAGTATGCTTGTGAAG

CCACAGATGAAGCATACTCAATGAATTGCTGCCCTGCCTACTGCCTCGGA

CTTCAAGGG-3'.

The sequence of P is: 5'-

(SEQ ID NO: 8)
CTGCAGTGCTGTTGACAGTGAGCGACGATAATATAACAGCAAGATTGTGA

AGCCACAGATGAATCTTGCTGTTATATTATCGCTGCCTACTGCCTCGGAC

TTCAAGGCTGCA-3'.

As seen in FIG. 1, the integrity of the plasmid was maintained after performing digestion and ligation reactions to create the recombinant plasmid with the desired shRNA inserts. The 109 bp sequence from the digestion analysis utilizing PstI confirms that the shRNA for the P insert was successful. The NS1 sequence is inserted after a double ligation so this same confirmation is not viable, but by observing the slight difference in band height for reactions 2 and 5 can be assumed to be the 114 bp NS1 insert, since the original sequence in that position is 107 bp. After Sanger Sequencing of the ligated plasmid, it was found that the resulting sequence originating from a primer binding within the NS1 insert showed homology to both inserts, as well as the spacer sequence in between them. From these results it can be concluded that the cloning of both inserts into the plasmid backbone has been completed successfully.

Example 2: Preparation and Characterization of Nanoparticles to Inhibit RSV Infection To inhibit RSV infection, triple-layered NPs involving both chitosan and lipids were designed and synthesized. A schematic representation of NP design showing the theoretical structure of the three-layered NPs is seen in FIG. 2A. TEM images of Chitosan-pDNA nanoparticles (third layer/core) (i), liposomes (second layer) (ii), liposomes encapsulated chitosan nanoparticles (iii) and liposomes loaded with chitosan nanoparticles and coated with an outer layer of chitosan (iv) and (v) revealed the successful coating (FIG. 2B). The particle size of different formulations was measured by dynamic light scattering (DLS) technique and it was found that the mean diameter of chitosan nanoparticles increases as the chitosan/pDNA ratio decreases (FIG. 2C). The Zeta Potential was also measured for the same samples at 25° C., by the same instrument (utilizing the Doppler electrophoresis technique). The results shown that the zeta potential increases as the chitosan/DNA ratio increases with a final Zeta potential value of +30 mV for 5:1 ratio.

The NPs were characterized for the plasmid encapsulation and integrity following synthesis, HR2D peptide release from the outer chitosan NP-layer in PBS and in 10% FBS and their cell (FIG. 3). First, chitosan-DNA nanoparticles were prepared by a complex coacervation method. In order to determine the optimal formulation, nanoparticles of different Chitosan/pDNA ratios were prepared and characterized. The binding of pDNA to chitosan for the formulations prepared herein was analyzed by gel electrophoresis. Complete encapsulation of DNA was observed when 2:1, 5:1 and 7:1 Chitosan:DNA ratios were used (FIG. 3A).

Chitosan/pDNA NPs were coated with a liposomal layer after co-extrusion of chitosan-pDNA NPs with pre-formed liposomes. This layer ensures the stability and integrity of the plasmid DNA and the endosomal escape and also allows for functionalization of the nanoparticle surface. The liposomal layer was then coated with another layer of chitosan complexed with fusion inhibitor HR2-D peptide. The release of the peptide from the outer layer was measured and it was found that 90% of the peptide was released within 10 minutes (FIG. 3B).

Biocompatibility studies revealed that in comparison with common used transfection reagents these NPs are much less toxic (FIG. 3C). FIG. 3C also shows that there is a slight decrease in viability of A549 cells in presence of the highest lipid concentration used herein (175 μg/ml). In comparison with other formulations that consist of cationic lipids for the effective delivery of DNA, the Chlipid-NPs are much less toxic.

Example 3: Inhibition of RSV rA2-L19F Infection by Plasmid Construct Expressing Short-Hairpin RNA for NS1 and P Genes To test for inhibition, A549 cells were transfected with a GFP plasmid construct expressing short-hairpin RNA for NS1 and P genes or scramble plasmid construct for 24 hours and infected with RFP-RSV-Ln19-A2 strain MOI 0.1 for 72 hours and imaged by fluorescent microscopy. Fluorescent microscopy images of RFP intensity quantified with ImageJ. The in vitro studies confirmed the effectiveness of the plasmid construct expressing short-hairpin RNA for NS1 and P proteins to inhibit RSV infection. As seen in FIG. 4, A549 cells transfected with the GFP-NS1-P construct resulted in significantly lower RFP expression in comparison with A549 cells transfected with GFP-scramble construct 72 hours post infection.

To test inhibition of RSV rA2-L19F infection by plasmid construct expressing short-hairpin RNA for NS1 and P genes, HEK 293 cells transfected with GFP plasmid construct expressing short-hairpin RNA for NS1 and P proteins or scramble plasmid construct for 24 hours and infected with RFP-RSV-Ln19-A2 strain MOI 0.1 for 72 hours were imaged by fluorescence microscopy. Pearson correlation coefficient was estimated using Imagej-Fiji. The successful inhibition of RFP-RSV infection by GFP-NS1/P short-hairpin expressing plasmid construct was also confirmed using HEK 293 cells (FIG. 5). The colocalization analysis for RFP and GFP showed that the Pearson correlation coefficient in the case that the HEK293 were transfected with the GFP-NS1/P construct was significantly lower compared to that of cells transfected with GFP-Scramble construct.

Example 4: Inhibition of RSV rA2-L19F Fusion by HR2D Peptide

To test inhibition of RSV rA2-L19F fusion by HR2D peptide, fluorescence microscopy images of A549 cells pre-treated with 5 or 20 μM HR2D peptide 30 min before RFP-RSV-Ln19-A2 infection MOI 0.1 for 24 hours. RFP intensity was quantified with ImageJ. The results showed the successful inhibition of RSV rA2-L19F fusion by HR2D peptide. A549 cells pre-treated with 5 or 20 μM HR2D peptide 30 min before infection showed significantly lower RFP expression indicating that HR2D peptide can block the RSV fusion (FIG. 6).

Example 5: Transfection Efficiency of NPs

To test transfection efficiency of NPs, HEK 293 cells were transfected with chitosan/GFP-pDNA, two layered nanoparticles and three layered nanoparticles, for 24 hours, and then imaged by fluorescence microscopy. The transfection efficiency of chitosan/GFP-pDNA, two-layered nanoparticles and three-layered nanoparticles in HEK 293 cells were also investigated. As seen in FIG. 7, the transfection efficiency of three layered-nanoparticles is higher compared to the transfection efficiency of chitosan/GFP-pDNA, or chitosan/GFP-pDNA coated with lipids and this is probably because of the positively charged chitosan layer on the surface of the NPs which improves the nanoparticle uptake. The chitosan-pDNA NP is also positively charged but its transfection efficiency is lower which may be due to DNA enzymatic degradation. The liposomal layer can protect the DNA from enzymatic cleavage and can improve the endosomal escape resulting in higher transfection efficiency.

Example 6: Targeting of NPs to RSV Infected Cells with Anti-ICAM Antibody

In order to improve the therapeutic potential of this nanosystem, targeted nanoparticles were designed that were functionalized with the anti-ICAM antibody to target the ICAM-1 receptor which is overexpressed in RSV infected epithelial cells. A549 cells infected with RFP-RSV with MOI 0.1 or MOI 1 were treated with either control nanoparticles (non-targeted) or anti-ICAM decorated FITC-labeled nanoparticles. Fluorescence microscopy images of A549 cells infected with RFP-RSV-Ln19-A2 strain MOI 0.1 or MOI for 24 hours and treated with FITC-labeled targeted or control NPs for 1 hour. RFP and FITC intensity quantified with ImageJ. As seen in FIG. 8, the uptake of targeted nanoparticles by RSV infected cells is significantly higher compared to that of control nanoparticles. Moreover, it was observed that for A549 cells infected with MOI 0.1 and treated with targeted nanoparticles, the nanoparticle uptake is very low for the non-transfected cells (yellow arrows) indicating that the targeted nanoparticles can selectively target RSV infected cells.

Example 7: Biodistribution of Triple-Layered NPs

To investigate the biodistribution of triple-layered NPs, studies were also conducted after intranasal administration of dual-labeled nanoparticles. Cy 5.5 was used to label the outer layer of chitosan and Cy 7 was used to label the chitosan complexed with PDNA on the nanoparticle core. Biodistribution was quantified from Cy7 and Cy 5 images of explanted organs 4, 24 and 48 hours post-injection. Biodistribution studies revealed the accumulation and prolonged retention of NPs primarily to the lungs for at least 48 hours post administration (FIG. 9).

BALB/c mice were injected intranasally with Chlipid-NPs (100 μg Chitosan/1.25 mg lipid per mouse). Cy7 labeled chitosan was used for the formation of the core of Chlipid-NPs while the chitosan on the surface was labeled with Cy5.5. The lipid bilayer was labeled with Rhodamine by incorporating 0.5 mol % Rhodamine-lipid in the liposomal bilayer (FIG. 18). The mice were sacrificed at different time points post injection (4, 24 and 48 hours) and the explanted organs were imaged using three different excitation/emission wavelengths to detect Cy7 (ex: 720 nm, em: 790 nm), Cy5.5 (ex: 660 nm, em: 710 nm), and Rhodamine (ex: 520 nm, em: 570 nm). Imaging results (FIG. 9) show that 4 hours post injection that the three layers of NPs are mainly accumulated in the lungs and that's an indication of nanoparticle integrity. 24 and 48 hours post injection, the lung Cy5.5 signal from the shell-chitosan is decreased to 33% and 20% of the initial signal, respectively while the rhodamine signal from the liposomal bilayer is decreased to 60% and 55%, respectively, indicating that the liposome-chitosan NP shell has been released from the outer chitosan shell at these time points. The Cy7, Cy5.5 and Rhodamine signals in the other organs is significantly lower compared to that in the lungs and the rhodamine (liposomal) signal is increased in the liver of mice 24 and 48 hours post injection, confirming the good mucoadhesive properties of these nanoparticles making them good candidates for intanasal and oral administration.

Example 8: Prophylactic Potential of NS1-P/HR2D NPs and the Free Combination of NS1-P/HR2D To determine whether Chlipid NPs exert an antiviral prophylactic potential in vivo, an immunocompromised BALB/c mouse model for respiratory syncytial virus infection was used. NS1-P/HR2D nanoparticles or free combination of NS1/P plasmid and HR2D peptide were administered intranasal 2 days before viral inoculation (RFP-RSV-Ln19-A2 strain). Mice were sacrificed 5 days post-infection and their explanted lungs were first imaged using IVIS system. RFP and GFP signal of lungs were quantified using imageJ. The results showed prophylactic potential of NS1-P/HR2D NPs. As seen in FIG. 10, the RFP lung signal of mice injected with NS1-P/HR2D nanoparticles is significantly lower compared to that of non-treated RSV-inoculated mice. The ex vivo results were further confirmed by fluorescent microscopy.

To test the prophylactic potential of NS1-P/HR2D NPs, fluorescence analysis of lung sections of mice administered with NS1-P-GFP/HR2D NPs or free NS1-P-GFP construct and HR2D was performed 2 days before RSV infection; mice were sacrificed 5 days post RFP-RSV-Ln19-A2 inoculation. As seen in FIG. 11, the RFP signal in the lungs of mice injected with NS1-P/HR2D nanoparticles is significantly lower compared to the RFP signal in the lungs of the mice treated with the free combination of NS1/P plasmid and HR2D peptide. Furthermore, the GFP expression on the lungs of the mice treated with NS1-P/HR2D nanoparticles confirms the successful in vivo transfection.

Lung sections of the groups were also subjected to H&E and PAS staining. H&E staining revealed that lung sections of NP treated mice had less inflammation in comparison with both non-treated and free-combo treated mice while the PAS staining revealed the reduced mucus accumulation to lungs of mice treated with nanoparticles (FIG. 12).

Example 9: Prophylactic Potential of NS1-P NPs, HR2D NPs and Dual NS1-P/HR2D NPs Then using the same mouse model, the prophylactic potential of nanoparticles encapsulated either the plasmid construct or the peptide or both was tested. Mice were treated with NPs two days before RSV inoculation and sacrificed 5 days post-infection. Their explanted lungs were first imaged using IVIS system and as seen in FIG. 13, RFP signal of the lungs of mice treated with nanoparticles encapsulated both the NS1-P pDNA construct and the HR2D peptide was significantly lower compared to RFP signals of the lungs of mice injected with either NS1-P nanoparticles or HR2D nanoparticles indicating that nanoparticles encapsulated both the construct and the peptide are more effective.

Fluorescence imaging of the lung sections further confirmed the higher prophylactic potential of NS1-P/HR2D loaded nanoparticles over the nanoparticles loaded with NS1-P or HR2D (FIG. 14A).

PAS staining of the lung sections showed reduced mucus accumulation (FIG. 14B). Also, these data show that nanoparticle treatment with plasmid containing shRNA against RSV NS1 and P, treatment with nanoparticles carrying HR2D peptide, or combination treatment results in a significant reduction in viral titer ex vivo (FIG. 14C). This data is in agreement with the in vivo qPCR data, which shows a reduction in viral transcripts NS1 and P as well, which corresponds to reduced viral replication (FIG. 14D). Together these data suggest the prophylactic use of these anti-RSV nanoparticles.

What is claimed is:

1. A nanoparticle, comprising:
   (a) first layer comprising chitosan and a heptad repeat (HR)2 peptide;
   (b) a second layer comprising a plurality of phospholipids forming a lipid bilayer; and (c) a third layer comprising chitosan, and a vector comprising a nucleic acid;

wherein the second layer is between the first layer and the third layer; wherein the first layer comprises an outer coat of the nanoparticle; and the third layer comprises an inner core of the nanoparticle.

2. The nanoparticle of claim 1, wherein the nucleic acid is small interfering RNA (siRNA) or short hairpin RNA (shRNA).

3. The nanoparticle of claim 1, wherein the vector is a dual expressing short hairpin RNA (shRNA) recombinant plasmid DNA.

4. The nanoparticle of claim 1, wherein the vector comprises a short hairpin RNA (shRNA) specific to respiratory syncytial virus's (RSV) non-structural 1 protein.

5. The nanoparticle of claim 1, wherein the vector comprises a short hairpin RNA (shRNA) specific to a respiratory syncytial virus (RSV) phosphoprotein.

6. The nanoparticle of claim 1, wherein the vector comprises a short hairpin RNA (shRNA) specific to respiratory syncytial virus's (RSV) non-structural 1 protein and an shRNA specific to a RSV phosphoprotein.

7. The nanoparticle of claim 1, wherein the first layer further comprises a targeting moiety.

8. The nanoparticle of claim 7, wherein the targeting moiety is an anti-ICAM antibody.

9. The nanoparticle of claim 2, wherein the siRNA or the shRNA is directed against respiratory syncytial virus (RSV) non-structural 1 protein (NS1) or RSV phosphoprotein (P).

10. The nanoparticle of claim 2, wherein the shRNA comprises: 5'-

(NS1a; SEQ ID NO: 9)
AGCAGCAATTCATTGAGTATGCTAGTGAAGCCACAGATGTAGCATACTCA

ATGAATTGCTGCC-3';

5'-

(NS1b; SEQ ID NO: 10)
ATGCATGTTATTACAAGTAGTTTAGTGAAGCCACAGATGTAAACTACTTG

TAATAACATGCAC-3';

5'-

(Pa; SEQ ID NO: 11)
AGATAATATAACAGCAAGATTTAGTGAAGCCACAGATGTAAATCTTGCTG

TTATATTATCG-3';

or
5'-

(Pb; SEQ ID NO: 12)
ACAGGGAACAAGCCCAATTATTTAGTGAAGCCACAGATGTAAATAATTGG

GCTTGTTCCCTGC-3'.

11. The nanoparticle of claim 2, wherein the siRNA or the shRNA inhibits the expression of a gene that encodes respiratory syncytial virus (RSV) non-structural 1 protein (NS1) and phosphoprotein (P).

12. The nanoparticle of claim 2, wherein the shRNA is directed against a sequence selected from one or more of the sequences of 5'-

(SEQ ID NO: 7)
CTGCTGTTGACAGTGAGCGAGGCAGCAATTCATTGAGTATGCTTGTGAAG

CCACAGATGAAGCATACTCAATGAATTGCTGCCCTGCCTACTGCCTCGGA

CTTCAAGGG-3' and 5'-

(SEQ ID NO: 8)
CTGCAGTGCTGTTGACAGTGAGCGACGATAATATAACAGCAAGATTGTGA

AGCCACAGATGAATCTTGCTGTTATATTATCGCTGCCTACTGCCTCGGAC

TTCAAGGCTGCA-3'.

13. The nanoparticle of claim 1, wherein the HR2 peptide consists of SEQ ID NO: 6.

14. The nanoparticle of claim 1, wherein the chitosan is ionically bonded to the HR2 peptide.

15. The nanoparticle of claim 1, wherein the ratio of the chitosan to the short hairpin RNA (shRNA) is about 2 to about 10.

16. The nanoparticle of claim 1, wherein the ratio of the chitosan to the short hairpin RNA (shRNA) is about 2, 5 or 7.

17. The nanoparticle of claim 1, wherein the nanoparticle is formulated for intravenous administration, intratracheal administration, intramuscular administration, subcutaneous administration, intranasal administration, oral administration, by inhalation or for direct injection or intravenous perfusion.

18. A pharmaceutical composition comprising a nanoparticle of claim 1 and a pharmaceutically acceptable carrier.

19. A method of delivering a nucleic acid to a subject, the method comprising administering to the subject an effective amount of a pharmaceutical composition comprising a nanoparticle of claim 1.

20. A method of treating or preventing a respiratory syncytial virus (RSV) infection in a subject, the method comprising administering to the subject an effective amount of a pharmaceutical composition comprising a nanoparticle of claim 1.

21. The method of claim 20, further comprising identifying a subject in need thereof.

22. The method of claim 20, wherein the subject is a human.

23. The method of claim 20, wherein the subject has RSV.

24. The method of claim 20, wherein the composition is administered to the subject intranasally, intravenously, by injection or orally.

25. The method of claim 20, further comprising administering ribavirin, palivizumab, a corticosteroid, an antibiotic or a combination thereof.

26. A method of inhibiting respiratory syncytial virus (RSV) replication by disrupting, impairing and/or displacing the non-structural 1 protein (NS1) - phosphoprotein (P) interaction, the method comprising contacting the nanoparticle of claim 1 with a cell.

27. A pharmaceutically acceptable vaccine composition comprising the nanoparticle of claim 1, wherein the nucleic acid is capable of eliciting an immune response in a host.

28. A method of vaccinating a mammal against a viral infection, the method comprising administering a nanoparticle of claim 1 in a pharmaceutically acceptable formulation to a human subject.

29. A method of upregulating cellular interferon, the method comprising contacting the nanoparticle of claim 1 with a cell.

30. A method of inhibiting the formation of mature RNA-dependent RNA polymerase, the method comprising contacting the nanoparticle of claim 1 with a cell.

31. A method of upregulating cellular interferon in a subject, the method comprising administering to the subject an effective amount of a pharmaceutical composition comprising a nanoparticle of claim 1.

32. A method of inhibiting the formation of mature RNA-dependent RNA polymerase in a subject, the method comprising administering to the subject an effective amount of a pharmaceutical composition comprising a nanoparticle of claim 1.

* * * * *

SEQUENCE LISTING

```
<160> NUMBER OF SEQ ID NOS: 12

<210> SEQ ID NO 1
<211> LENGTH: 35
<212> TYPE: PRT
```

<213> ORGANISM: Artificial Sequence
<220> FEATURE:
<223> OTHER INFORMATION: Synthetic construct

<400> SEQUENCE: 1

```
Phe Asp Ala Cys Ile Ser Gln Val Asn Glu Cys Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35
```

<210> SEQ ID NO 2
<211> LENGTH: 35
<212> TYPE: PRT
<213> ORGANISM: Artificial Sequence
<220> FEATURE:
<223> OTHER INFORMATION: Synthetic construct

<400> SEQUENCE: 2

```
Phe Asp Ala Ser Ile Ser Gln Val Asn Glu Lys Ile Asn Gln Ser Leu
1               5                   10                  15

Ala Phe Ile Cys Lys Ser Asp Glu Leu Leu Cys Asn Val Asn Ala Gly
            20                  25                  30

Lys Ser Thr
        35
```

<210> SEQ ID NO 3
<211> LENGTH: 35
<212> TYPE: PRT
<213> ORGANISM: Artificial Sequence
<220> FEATURE:
<223> OTHER INFORMATION: Synthetic construct

<400> SEQUENCE: 3

```
Phe Asp Ala Cys Ile Ser Gln Val Asn Glu Cys Ile Asn Gln Ser Leu
1               5                   10                  15

Ala Phe Ile Cys Lys Ser Asp Glu Leu Leu Cys Asn Val Asn Ala Gly
            20                  25                  30

Lys Ser Thr
        35
```

<210> SEQ ID NO 4
<211> LENGTH: 15
<212> TYPE: PRT
<213> ORGANISM: Artificial Sequence
<220> FEATURE:
<223> OTHER INFORMATION: Synthetic construct

<400> SEQUENCE: 4

```
Gly Ile Ser Gln Val Asn Glu Gly Lys Ser Asp Glu Leu Leu Gly
1               5                   10                  15
```

<210> SEQ ID NO 5
<211> LENGTH: 17
<212> TYPE: PRT
<213> ORGANISM: Artificial Sequence
<220> FEATURE:
<223> OTHER INFORMATION: Synthetic construct

<400> SEQUENCE: 5

```
Gly Cys Ile Ser Gln Val Asn Glu Cys Lys Ser Asp Glu Leu Leu Cys
1               5                   10                  15
```

Gly

<210> SEQ ID NO 6
<211> LENGTH: 28
<212> TYPE: PRT
<213> ORGANISM: Artificial Sequence
<220> FEATURE:
<223> OTHER INFORMATION: Synthetic construct

<400> SEQUENCE: 6

Asp Ala Cys Ile Ser Gln Val Asn Glu Cys Ile Asn Gln Ser Leu Ala
1               5                   10                  15

Phe Ile Cys Lys Ser Asp Glu Leu Leu Cys Asn Thr
            20                  25

<210> SEQ ID NO 7
<211> LENGTH: 109
<212> TYPE: DNA
<213> ORGANISM: Artificial Sequence
<220> FEATURE:
<223> OTHER INFORMATION: Synthetic construct

<400> SEQUENCE: 7
ctgctgttga cagtgagcga ggcagcaatt cattgagtat gcttgtgaag ccacagatga    60
agcatactca atgaattgct gccctgccta ctgcctcgga cttcaaggg               109

<210> SEQ ID NO 8
<211> LENGTH: 112
<212> TYPE: DNA
<213> ORGANISM: Artificial Sequence
<220> FEATURE:
<223> OTHER INFORMATION: Synthetic construct

<400> SEQUENCE: 8
ctgcagtgct gttgacagtg agcgacgata atataacagc aagattgtga agccacagat    60
gaatcttgct gttatattat cgctgcctac tgcctcggac ttcaaggctg ca            112

<210> SEQ ID NO 9
<211> LENGTH: 63
<212> TYPE: DNA
<213> ORGANISM: Artificial Sequence
<220> FEATURE:
<223> OTHER INFORMATION: Synthetic construct

<400> SEQUENCE: 9
agcagcaatt cattgagtat gctagtgaag ccacagatgt agcatactca atgaattgct    60
gcc                                                                  63

<210> SEQ ID NO 10
<211> LENGTH: 63
<212> TYPE: DNA
<213> ORGANISM: Artificial Sequence
<220> FEATURE:
<223> OTHER INFORMATION: Synthetic construct

<400> SEQUENCE: 10
atgcatgtta ttacaagtag tttagtgaag ccacagatgt aaactacttg taataacatg    60
cac                                                                  63

<210> SEQ ID NO 11
<211> LENGTH: 61
<212> TYPE: DNA
<213> ORGANISM: Artificial Sequence

```
<220> FEATURE:
<223> OTHER INFORMATION: Synthetic construct

<400> SEQUENCE: 11
agataatata acagcaagat ttagtgaagc cacagatgta aatcttgctg ttatattatc    60
g                                                                  61

<210> SEQ ID NO 12
<211> LENGTH: 63
<212> TYPE: DNA
<213> ORGANISM: Artificial Sequence
<220> FEATURE:
<223> OTHER INFORMATION: Synthetic construct

<400> SEQUENCE: 12
acagggaaca agcccaatta tttagtgaag ccacagatgt aaataattgg gcttgttccc    60
tgc                                                                63
```